(12) United States Patent
Steenlage

(10) Patent No.: US 7,144,424 B2
(45) Date of Patent: Dec. 5, 2006

(54) METHOD AND APPARATUS FOR RECONSTRUCTING A LIGAMENT

(75) Inventor: Eric S. Steenlage, Atlanta, GA (US)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 10/412,883

(22) Filed: Apr. 14, 2003

(65) Prior Publication Data

US 2004/0006389 A1    Jan. 8, 2004

Related U.S. Application Data

(60) Provisional application No. 60/372,324, filed on Apr. 12, 2002.

(51) Int. Cl.
*A61F 2/08* (2006.01)
(52) U.S. Cl. ................ 623/13.14; 623/13.17; 606/72; 606/151
(58) Field of Classification Search ... 623/13.11–13.14
See application file for complete search history.

(56) References Cited

U.S. PATENT DOCUMENTS

| 4,605,414 | A | * | 8/1986 | Czajka | 128/898 |
| 5,320,115 | A | | 6/1994 | Kenna | 128/898 |
| 5,645,547 | A | | 7/1997 | Coleman | 606/73 |
| 5,665,090 | A | | 9/1997 | Rockwood et al. | 606/80 |
| 5,891,146 | A | * | 4/1999 | Simon et al. | 606/71 |
| 6,099,530 | A | * | 8/2000 | Simonian et al. | 606/75 |
| 6,113,604 | A | * | 9/2000 | Whittaker et al. | 606/72 |
| 6,132,433 | A | | 10/2000 | Whelan | 606/72 |

* cited by examiner

*Primary Examiner*—Corrine McDermott
*Assistant Examiner*—Christopher D Prone
(74) *Attorney, Agent, or Firm*—St. Onge Steward Johnston & Reens LLC

(57) ABSTRACT

A new approach for reconstructing a ligament, the new approach comprising: creating a bone tunnel within a host bone, the bone tunnel having a proximal end and a distal end, and defining a central axis extending from the proximal end to the distal end; creating an intervening layer of bone between the central axis of the bone tunnel and a rigid portion of the host bone, the intervening layer having a first side and a second side in opposition to one another, the first side of the intervening layer facing toward the central axis of the bone tunnel and the second side of the intervening layer facing toward the rigid portion of the surrounding host bone; and compressing the intervening layer of bone against a graft ligament positioned within the bone tunnel.

12 Claims, 28 Drawing Sheets

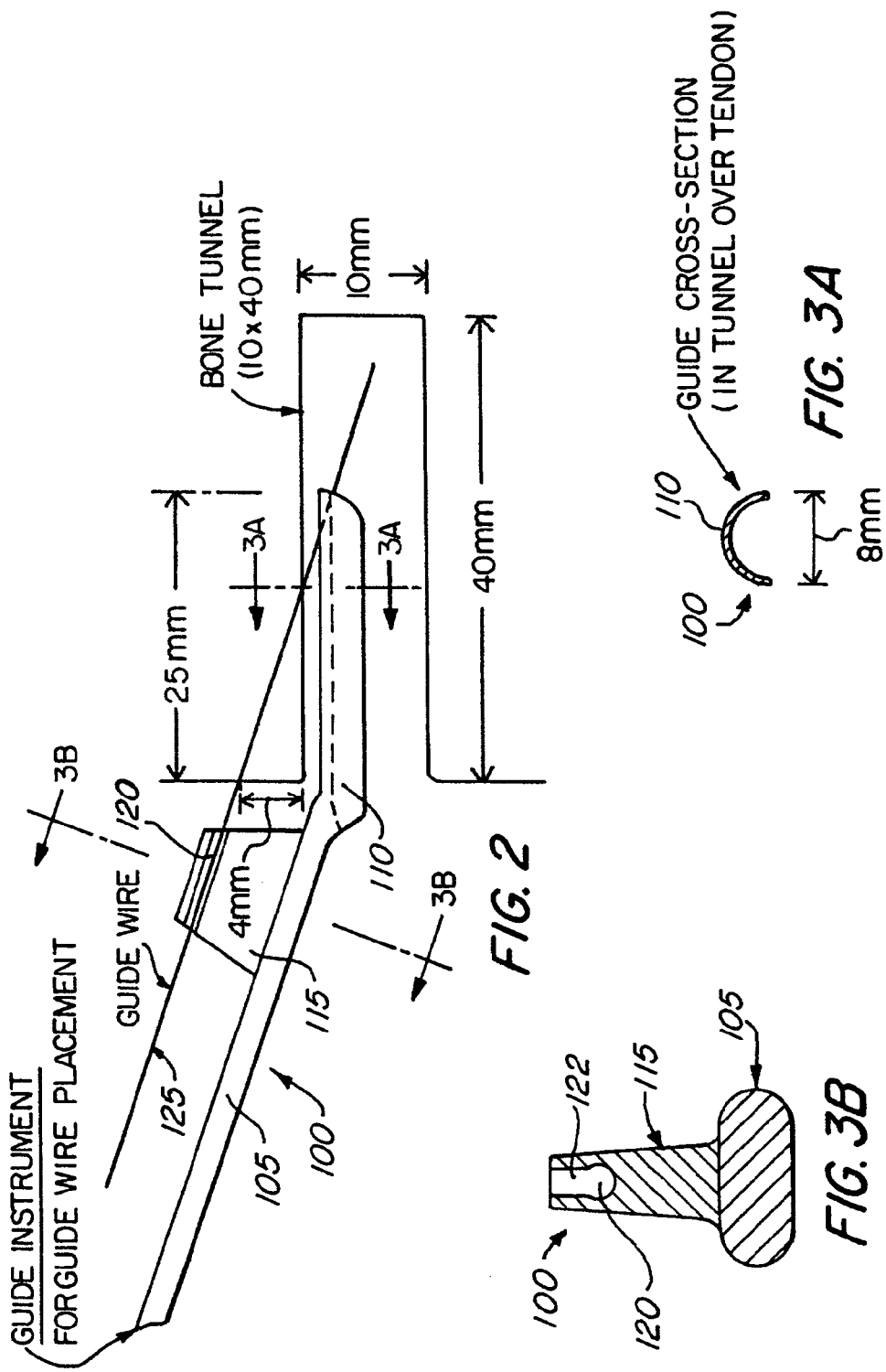

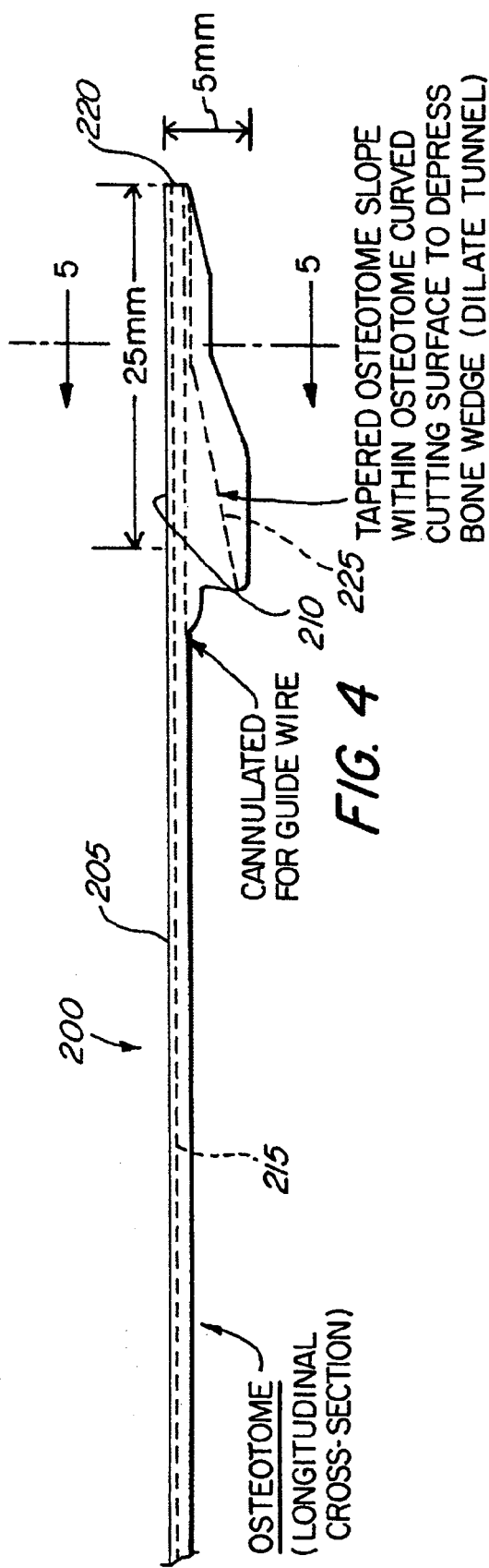
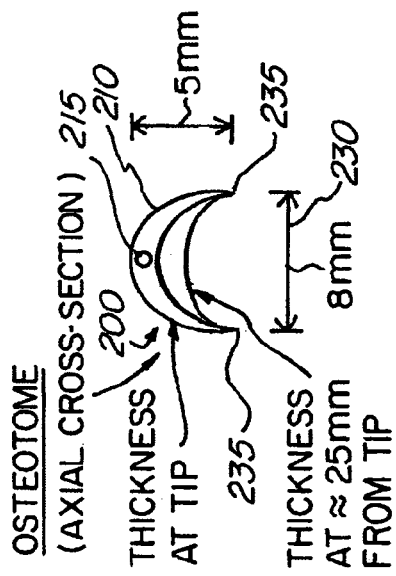
FIG. 4
FIG. 5

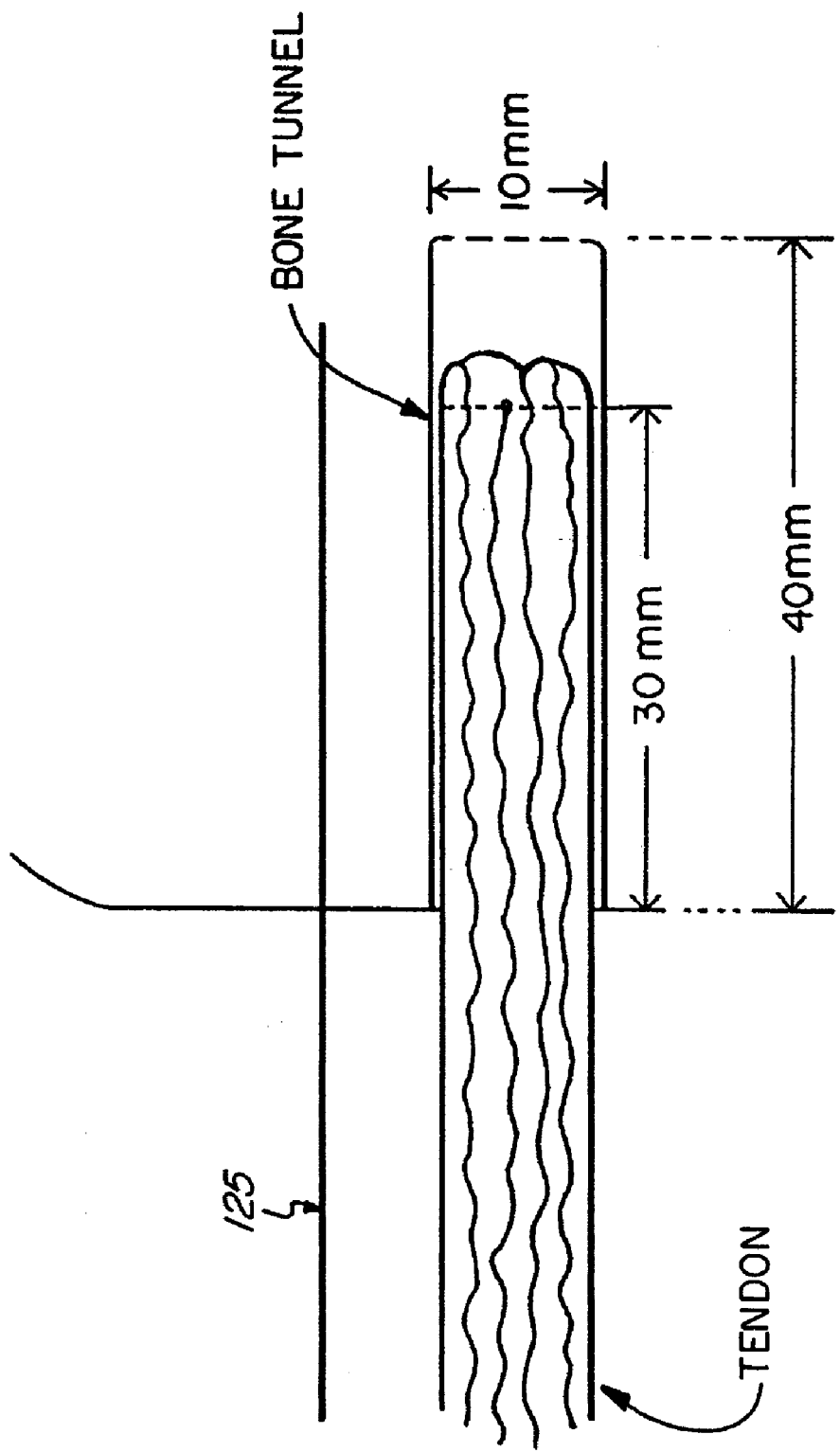

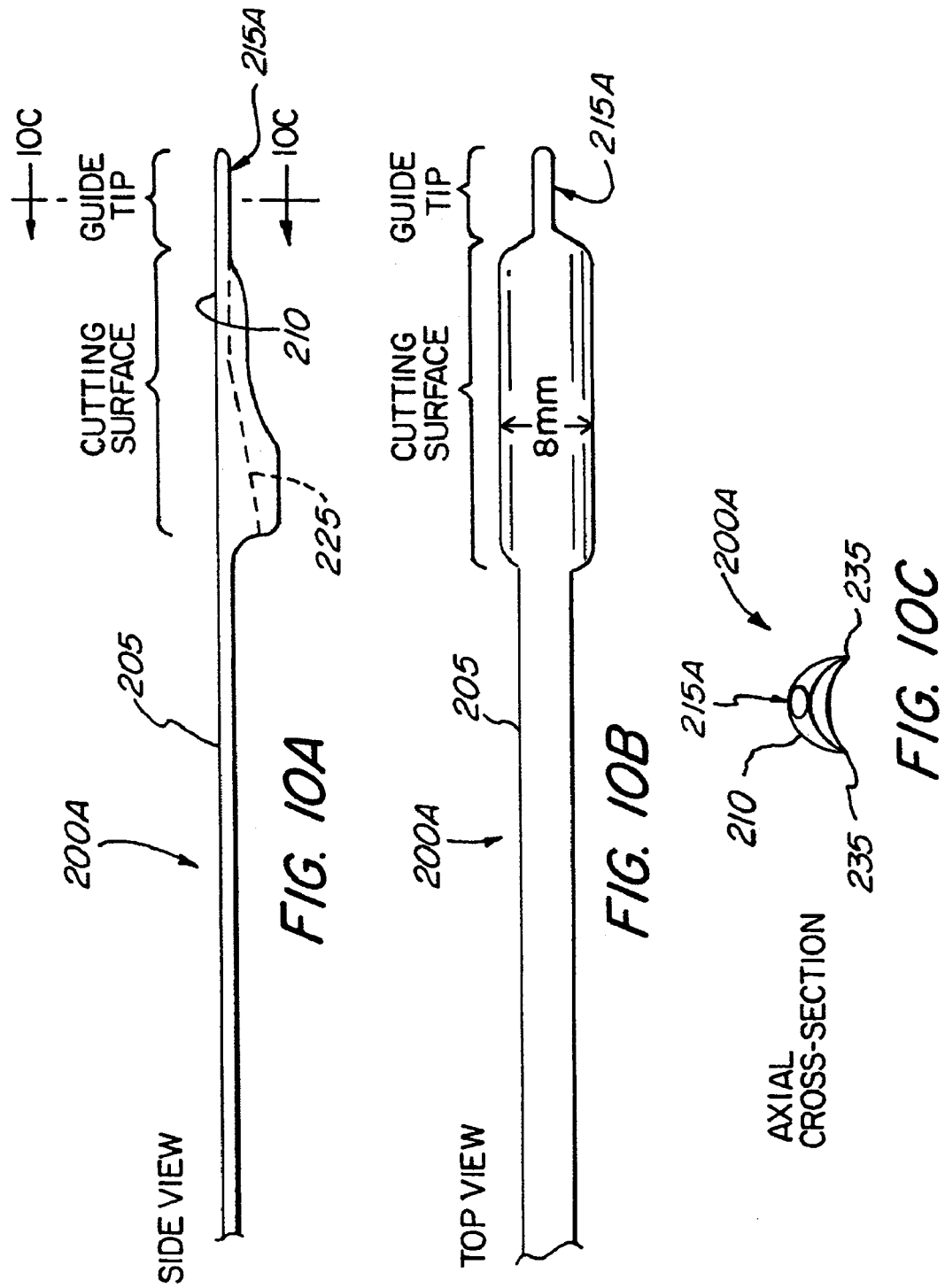

METHOD AND APPARATUS FOR RECONSTRUCTING A LIGAMENT

REFERENCE TO PENDING PRIOR PATENT APPLICATION

This patent application claims benefit of now abandoned prior U.S. Provisional Patent Application Ser. No. 60/372,324, filed Apr. 12, 2002 by Eric S. Steenlage et al. for METHOD AND APPARATUS FOR RECONSTRUCTING A LIGAMENT, which patent application is hereby incorporated herein by reference.

FIELD OF THE INVENTION

This invention relates to surgical methods and apparatus in general, and more particularly to surgical methods and apparatus for reconstructing a ligament.

BACKGROUND OF THE INVENTION

Stable healing of a tendon graft to the adjacent bone is generally considered to be the single most important factor in any type of tendon or ligament reconstruction. Successful incorporation of the graft is primarily dependent on two factors. First, the graft must be fixed in such a way as to maximize the contact area between the graft and the bone, thereby providing the greatest amount of surface area for graft incorporation. Second, the graft fixation must be stable, minimizing the amount of motion between graft and bone. This will minimize the amount of weak fibrous tissue that forms at the bone-graft interface and maximize the degree to which a more stable bone-soft tissue interface develops at the point of bone-graft contact.

One of the specific areas in which this problem of bone-to-tendon graft healing has received the greatest amount of attention is in the area of cruciate ligament reconstruction. Anterior cruciate ligament (ACL) reconstruction in particular has been an area of intense interest. Graft fixation techniques for ACL reconstruction have become an area of intense debate, research, and product development. Graft fixation during the ACL reconstruction procedure will be used as an example to demonstrate the properties of the new fixation concept described here. Other applications, such as but not limited to other types of ligament reconstruction, are obviously possible as well.

One of the graft fixation techniques that has become increasingly popular is interference screw fixation. Many recent advances have been made in improving the pullout strength of tendon grafts when using interference screw fixation. Better tunnel location, tunnel compaction, tighter graft/tunnel fit, improved graft preparation/suturing techniques, and the use of longer, biodegradable screws have all contributed to nearly doubling the pullout strengths obtained from the initial interference fixation studies.

One of the fundamental problems associated with interference screw fixation has remained unchanged, however. More specifically, the presence of the interference screw on one side of the graft limits the bone/graft contact to only a portion of the graft's circumferential area. Histology studies have suggested that in the long term, the most stable bony ingrowth of the graft into the surrounding bone occurs primarily at the outer rim of the bone tunnel. With interference screw fixation this ingrowth is possible only on the side of the graft that is in direct contact with bone; the other half of the graft contacts only the screw and hence is not available for bony ingrowth.

Thus, in practice, there is effectively no bony ingrowth where the interference screw intervenes between the tendon graft and the host bone.

The use of bioresorbable screws may provide the opportunity for additional bone ingrowth after the bioresorbable screw has been resorbed. However, the timing, extent and type of ingrowth occurring on the screw side of the tendon, after the bioresorbable screw has been resorbed, has yet to be fully determined.

In addition to the foregoing, spinning of the tendon graft during insertion of the interference screw is a well-documented problem that is difficult to control once it has begun. This "tendon spin" can damage the graft and result in impingement and less-than-ideal graft positioning, possibly affecting the clinical results.

As a result of the foregoing, one of the arguments for extra-cortical or non-aperture types of fixation, such as graft suspension systems like the ENDOBUTTON™ system or cross-pinning, is that there is, theoretically, circumferential bone/tendon graft contact, making full circumferential bony ingrowth at least a theoretical possibility. However, such distal types of fixation are often less stiff and provide less stable fixation of the graft in the bone tunnel. This decreased stability and subsequent increased graft-tunnel motion may inhibit the formation of a stable graft-bone interface, interfering with graft incorporation into the adjacent bone and the creation of a functionally stable ligament reconstruction. In addition, this increased graft motion has been associated with widening of the bone tunnel. This tunnel widening, thought to be due to the so-called "windshield wiper" and "bungee-cord" motion of the graft within the bone tunnel, is indicative of an unstable graft-bone construct that is prone to failure.

Improving the biologic potential of graft fixation by increasing the native bone/tendon graft contact area, while still compressing the graft and closing the bone tunnel using interference fixation, would be a desirable goal. Maintaining adequate fixation strength when using any new technique is obviously critical, and improving fixation strength while also improving the biologic properties of the fixation method would obviously represent a significant improvement in graft fixation.

This application describes a new method and apparatus to achieve these goals.

SUMMARY OF THE INVENTION

The preferred form of the present invention includes numerous novel aspects. Among these are:

(1) creation of an intervening layer of bone between the tendon graft and the compressing interference screw device;

(2) allows insertion of the interference screw compression device at an oblique angle, contacting and at least partially penetrating the end of the tendon graft deep in the bone tunnel with the tip of the device—this creates the possibility of tangential interstitial fixation of the graft; and (3) development of a new interference compression device specifically designed to maximize the biomechanical and biological advantages made possible with the two concepts listed above.

A significant aspect of this new graft fixation system is the creation of a layer of native bone between the tendon graft in the bone tunnel and the interference screw used for fixation. The graft used may be a soft tissue tendon or tendon with attached bone block(s), etc. More particularly, with the present invention, using reconstruction of the ACL as an example, the tibial and femoral bone tunnels are first prepared and then the tendon is passed into them in the usual manner. Femoral fixation will be described as an example here. A small cut is made in the bone directly above, and in line with, the femoral bone tunnel so as to create an intervening wedge-shaped layer of bone. This is preferably done with a specifically designed osteotome, with or without a guide system, to ensure maximum control during the creation of the intervening bone layer. The intervening layer of bone can be created in one of two ways.

The bone layer can be created so that it is wedge-shaped, thickest at the outer end of the bone tunnel, and converging toward, and preferably converging with, the bone tunnel at the deep end of the tunnel. An interference screw device is then placed into the osteotomy site, with or without the use of a guidewire. The interference device is advanced so that the underlying layer of bone is compressed into the bone tunnel that contains the tendon graft, thereby achieving interference fixation while surrounding the tendon graft with native bone. The interference device is preferably advanced into the bone tunnel to a depth where the screw tip meets, and preferably passes at least part way through, the end of the tendon graft in the tunnel. This enhances the biomechanical fixation strength of the graft-bone tunnel construct.

Alternatively, the intervening layer of bone can be created with the osteotomy cut being made in a parallel fashion with the underlying bone tunnel, creating a more uniform intervening layer of bone between the graft and fixation device. Thus, in this form of the invention, the interference screw will be advanced substantially parallel to, and will not engage, the graft ligament.

The technique of the present invention may be used alone, as the sole manner of fixing the graft ligament in the bone tunnel, or it may be used in combination with other non-aperture fixation devices such as the ENDOBUTTON™ system or cross-pinning, etc. Such hybrid fixation utilizes the reproducible biomechanical fixation these devices provide while compressing the graft and closing the bone tunnel using this new method.

When used with tendon grafts with attached bone blocks, such as bone-patella tendon-bone (BPTB) grafts, fixation will also be enhanced by "locking" the bone block deep in the bone tunnel, deep to the bone wedge layer that has been compressed into the graft by the interference device. When using either soft tissue grafts or grafts with attached bone blocks, stable fixation at the aperture of the bone tunnel, necessary to minimize the previously described motion of the tendon within the tunnel, is provided.

This new approach also helps solve the problem of providing aperture fixation when using BPTB grafts. More particularly, the tendinous portions of these grafts are usually longer than the normal intra-articular length of the native cruciate ligament. As a result, reconstruction using a BPTB graft usually requires that the bone plug either be fixed deep in the bone tunnel, making aperture fixation impossible, or the bone plug on one end of the tendon must be doubled back on itself prior to graft passage, which presents technical difficulties. The new approach presented here provides fixation of the tendon block deep in the bone tunnel while also providing stable aperture fixation.

Significantly, the foregoing new fixation technique retains the established benefits of the interference fixation techniques currently widely utilized in ligament reconstruction. At the same time, creation of an intervening layer of bone to provide circumferential bone/tendon graft contact significantly enhances the potential for bone ingrowth into the tendon graft, which is important for clinically successful results.

A fixation device specific for this technique may enhance the benefits of the new approach described above. Several different device designs are possible. One such device is essentially a combination of a screw and pin. The screw portion, essentially similar to an interference screw, enables introduction of the implant while providing compression fixation. The modified tip of the device, of which several configurations are possible, is designed to enhance fixation strength by providing a combination of oblique interstitial transfixation and compression of the end of the tendon graft deep in the bone tunnel.

In one form of the invention, there is provided a method for reconstructing a ligament, the method comprising: creating a bone tunnel within a host bone, the bone tunnel having a proximal end and a distal end, and defining a central axis extending from the proximal end to the distal end; creating an intervening layer of bone between the central axis of the bone tunnel and a rigid portion of the host bone, the intervening layer having a first side and a second side in opposition to one another, the first side of the intervening layer facing toward the central axis of the bone tunnel and the second side of the intervening layer facing toward the rigid portion of the host bone; and compressing the intervening layer of bone against a graft ligament positioned within the bone tunnel.

In another form of the invention, there is provided apparatus for reconstructing a ligament, the apparatus comprising: creation means for creating an intervening layer of bone between a central axis of a bone tunnel and a rigid portion of the host bone, the intervening layer of bone having a first side and a second side in opposition to one another, the first side of the intervening layer facing toward the central axis of the bone tunnel and the second side of the intervening layer facing toward the rigid portion of the host bone; and compression means for compressing the intervening layer of bone against a graft ligament positioned within the bone tunnel.

In another form of the invention, there is provided an osteotome for dividing bone adjacent to a bone tunnel, the osteotome comprising: a handle having a proximal end and a distal end, and defining a longitudinal axis extending from the proximal end to the distal end; a blade disposed at the distal end of the handle, the blade having a first side and a second side in opposition to one another, the first side being configured for placement toward the bone tunnel; and at least one of the handle and the blade defining a lumen therethrough, the lumen being substantially parallel to the longitudinal axis of the handle; wherein the osteotome is configured for advancement over a guide device chosen from a group consisting of a guide pin and a guidewire, the guide device extending from bone adjacent to the bone tunnel, the osteotome is advanced into the bone, and the osteotome is withdrawn from the bone so as to create an opening through the bone adjacent to the bone tunnel with an intervening layer of bone therebetween.

In another form of the invention, there is provided an osteotome system for dividing bone adjacent to a bone tunnel, the osteotome system comprising: a guide instrument for placement of a guide device chosen from a group consisting of a guide pin and a guidewire adjacent to the bone tunnel, the guide instrument comprising: a handle having a proximal end and a distal end, and defining a first longitudinal axis extending from the proximal end to the distal end; a foot extending from the distal end of the handle, the foot having a first surface and a second surface in opposition to one another, the first surface configured for placement into the bone tunnel toward a center region thereof, and the second surface configured for placement into the bone tunnel toward a wall thereof; and an aimer extending from a given surface of the handle, the aimer defining a bore at a given height from the second surface of the handle, and the bore configured to align the guide device through the bone adjacent to the bone tunnel toward the center region of the bone tunnel; and an osteotome for dividing bone adjacent to the bone tunnel, the osteotome comprising: a handle having a proximal end and a distal end, and defining a longitudinal axis extending from the proximal end to the distal end; a blade disposed at the distal end of the handle, the blade having a first side and a second side in opposition to one another, the first side being configured for placement toward the bone tunnel; and at least one of the handle and the blade defining a lumen therethrough, the lumen being substantially parallel to the longitudinal axis of the handle; wherein the osteotome is configured for advancement over the guide device, the guide device extending from the bone adjacent to the bone tunnel, the osteotome is advanced into the bone, and the osteotome is withdrawn from the bone so as to create an adjacent to the bone tunnel with an intervening layer of bone therebetween.

In another form of the invention, there is provided a system for reconstructing a ligament, the system comprising: a guide instrument for placement of a guide device chosen from a group consisting of a guide pin and a guidewire adjacent to the bone tunnel, the guide instrument comprising: a handle having a proximal end and a distal end, and defining a first longitudinal axis extending from the proximal end to the distal end; a foot extending from the distal end of the handle, the foot having a first surface and a second surface in opposition to one another, the first surface configured for placement into the bone tunnel toward a center region thereof, and the second surface configured for placement into the bone tunnel toward a wall thereof; and an aimer extending from a given surface of the handle, the aimer defining a bore at a given height from the second surface of the handle, and the bore configured to align the guide device through the bone adjacent to the bone tunnel toward the center region of the bone tunnel; an osteotome for dividing bone adjacent to the bone tunnel, the osteotome comprising: a handle having a proximal end and a distal end, and defining a longitudinal axis extending from the proximal end to the distal end; a blade disposed at the distal end of the handle, the blade having a first side and a second side in opposition to one another, the first side being configured for placement toward the bone tunnel; and at least one of the handle and the blade defining a lumen therethrough, the lumen being substantially parallel to the longitudinal axis of the handle; wherein the osteotome is configured for advancement over the guide device, the guide device extending from the bone adjacent to the bone tunnel, the osteotome is advanced into the bone, and the osteotome is withdrawn from the bone so as to create an opening through the bone adjacent to the bone tunnel with an intervening layer of bone therebetween; and an interference compression device for compressing the intervening layer of bone against a graft ligament positioned within the bone tunnel.

In another form of the invention, there is provided a guide device for making a drill hole that will serve as a guide for a specially designed osteotome with a guide tip at its distal end; the drill hole controls the length and shape of the intervening bone layer that is created by the osteotome when the osteotome has its guide tip advanced down the guide hole in the bone, whereby to control advancement of the osteotome into the bone.

In another form of the invention, there is provided an interference screw comprising: a shaft having a distal end and a proximal end; and at least one helical thread extending between said distal end and said proximal end; said distal end of said shaft being configured for piercing a graft ligament.

In another form of the invention, there is provided a construct for a ligament reconstruction, the construct comprising: a host bone having a bone tunnel formed therein, the bone tunnel having a proximal end and a distal end, and the bone tunnel defining a central axis extending from the proximal end to the distal end; a graft ligament disposed within the bone tunnel; the host bone having an opening formed therein adjacent to the bone tunnel, the opening forming an intervening layer of bone between the central axis of the bone tunnel and a rigid portion of the host bone, the intervening layer having a first side and a second side in opposition to one another, the first side of the intervening layer facing toward the central axis of the bone tunnel and the second side of the intervening layer facing toward the rigid portion of the host bone, and the opening configured to incompletely break away the intervening layer of bone from the rigid portion of the host bone so as to hinge inwardly toward the central axis of the bone tunnel and maintain bone-to-bone opposition between the intervening layer and the rigid portion of the host bone; and an interference compression device positioned between the second side of the intervening layer of bone and the rigid portion of the host bone so as to compress the intervening layer of bone against the graft ligament positioned within the bone tunnel.

In another form of the invention, there is provided an osteotome system for dividing bone adjacent to a bone tunnel, the osteotome system comprising: a handle having a proximal end and a distal end, and defining a longitudinal axis extending from the proximal end to the distal end; a blade disposed at the distal end of the handle, the blade having a first side and a second side in opposition to one another, the first side being configured for placement toward the bone tunnel; and a guide tip extending distally away from the blade; wherein the osteotome is configured for advancement into the bone by advancing the guide tip into a guide hole formed in the bone adjacent to the bone tunnel, with the osteotome being advanced into the bone, and then withdrawn from the bone, so as to create an opening through the bone adjacent to the bone tunnel with an intervening layer of bone therebetween.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 2 is a schematic side view of a guide which may be used to establish the path for the osteotome to follow when forming the bone wedge;

FIG. 3A is a sectional view taken along line 3A—3A of FIG. 2;

FIG. 3B is a sectional view taken along line 3B—3B of FIG. 2;

FIG. 4 is a schematic view of a design for a novel osteotome for use in creating a wedge of bone above the femoral tunnel;

FIG. 5 is a sectional view taken along line 5—5 of FIG. 4;

FIGS. 7A, 7B, 7C and 7D show alternative concepts for creating bone layers with alternative geometries;

FIG. 10A is a schematic side view of an alternative novel osteotome design, incorporating many of the features of the osteotome described in FIGS. 4 and 5, but having a distal guide tip designed to follow a pre-drilled guide hole instead of being cannulated to travel over a guidewire;

FIG. 10B is a schematic side view of the novel osteotome shown in FIG. 10A;

FIG. 10C is a schematic sectional view taken along line 10C—10C of FIG. 10A.

DETAILED DESCRIPTION OF THE PREFERRED EMBODIMENTS

Figure 1:
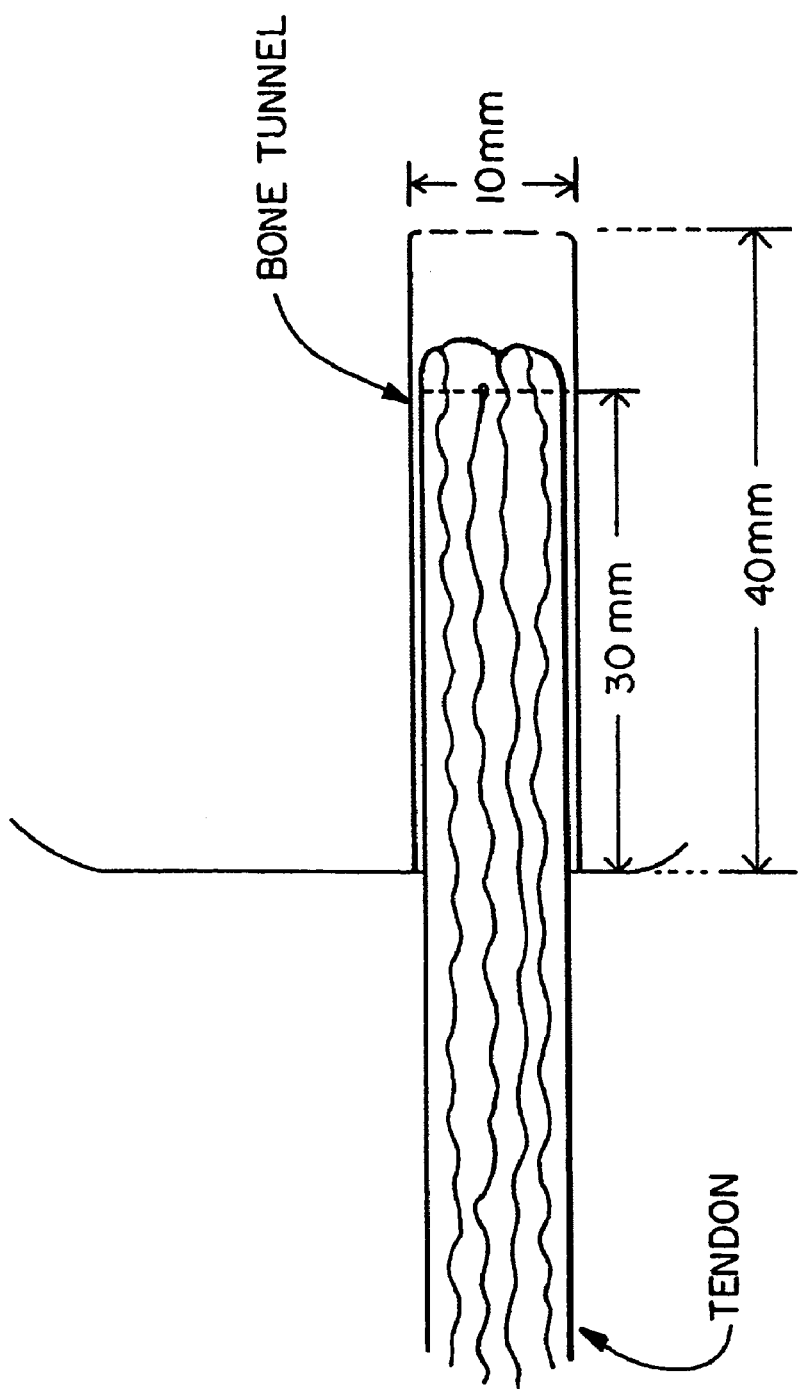
FIG. 1 is a schematic side view showing a graft ligament in a bone tunnel.

This detailed description will again use the femoral side of an ACL reconstruction as an example of the multiple uses of this new concept; however, as noted above, this application is intended to be merely exemplary and the invention may be used on the tibial side of an ACL reconstruction, or in connection with some other type of ligament reconstruction, etc.

Using this new approach, the initial steps in the ACL reconstruction are unchanged from that usually done when using interference screws for graft fixation. Autografts or allografts, with or without attached bone blocks, can be utilized. Arthroscopic examination of the knee is done in the standard fashion, with debridement of the residual anterior cruciate ligament tissue and preparation of the femoral notch. The tendon graft is harvested, prepared, and measured. The bone tunnels are made in the tibia and femur in the standard fashion, typically using one of the commercially available guidance systems. As always, care should be taken with tunnel and tendon preparation, optimizing tunnel location and size, and utilizing appropriate tendon suturing methods. The graft ligament is then inserted into the bone tunnels. See FIG. 1, which shows the tendon graft inserted into the bone tunnel formed in the bottom of the femur and extending back into the interior of the knee joint.

The present invention diverges from the standard practice once the tendon has been passed into the bone tunnels.

A significant aspect of the present invention is (i) the creation of a small, preferably wedge-shaped, layer of bone between the tendon and the wall of the host bone, and then (ii) the compression of this layer of bone against the tendon using an interference compression device set outside, and bearing against, the intervening layer of bone. The layer of bone is incompletely broken away from its native position, hinging downwards while maintaining some of the bone-to-bone apposition on its edges. With this new method, nearly the entire tendon graft is compressed by native, cancellous bone. All of the benefits of interference fixation are retained, such as exclusion of synovial fluid from the bone tunnel; at the same time, the area of contact between the graft and the host bone is increased.

As described here, the creation of the intervening bone layer can have a positive impact on the effectiveness of the ligament reconstruction procedure. Therefore, the nature and use of the osteotome used to create the bone layer can obviously have a significant impact on the successful execution of this procedure. To this end, a unique osteotome specific for this system will now be described, although the use of other designs and methods may also be utilized to practice the present invention.

One possible osteotome system comprises a guide 100 (FIGS. 2, 3A and 3B) and an osteotome 200 (FIGS. 4 and 5). Guide 100 is used to establish the path that is to be followed by osteotome 200, and osteotome 200 is then used to create the bone layer (preferably wedge-shaped) that is displaced by the interference screw so as to fix the graft ligament to the host bone. The present invention may also be practiced without the guide 100, or without the osteotome 200, or without both; however, it is believed that the use of guide 100 and osteotome 200 facilitate practicing of the present invention.

More particularly, and looking now at FIGS. 2 and 3, guide instrument 100 preferably comprises a handle 105 having a foot 110 and an aimer 115. Foot 110 has a semicircular cross-section (FIG. 3A) so that it will fit between the graft ligament and the wall of the bone tunnel. Aimer 115 includes a bore 120 adapted to receive and guide a guide pin or guidewire 125, which will itself subsequently guide osteotome 200. A slot 122 (FIG. 3B) connects bore 120 to the top of aimer 115, so that guidewire 125 can be released from aimer 115, i.e., when the distal end of the guidewire is deployed in a bone and guide instrument 100 is to be withdrawn proximally. The geometry of guide 100 ensures that the osteotome 200 is driven in line with the tunnel.

Figure 6:
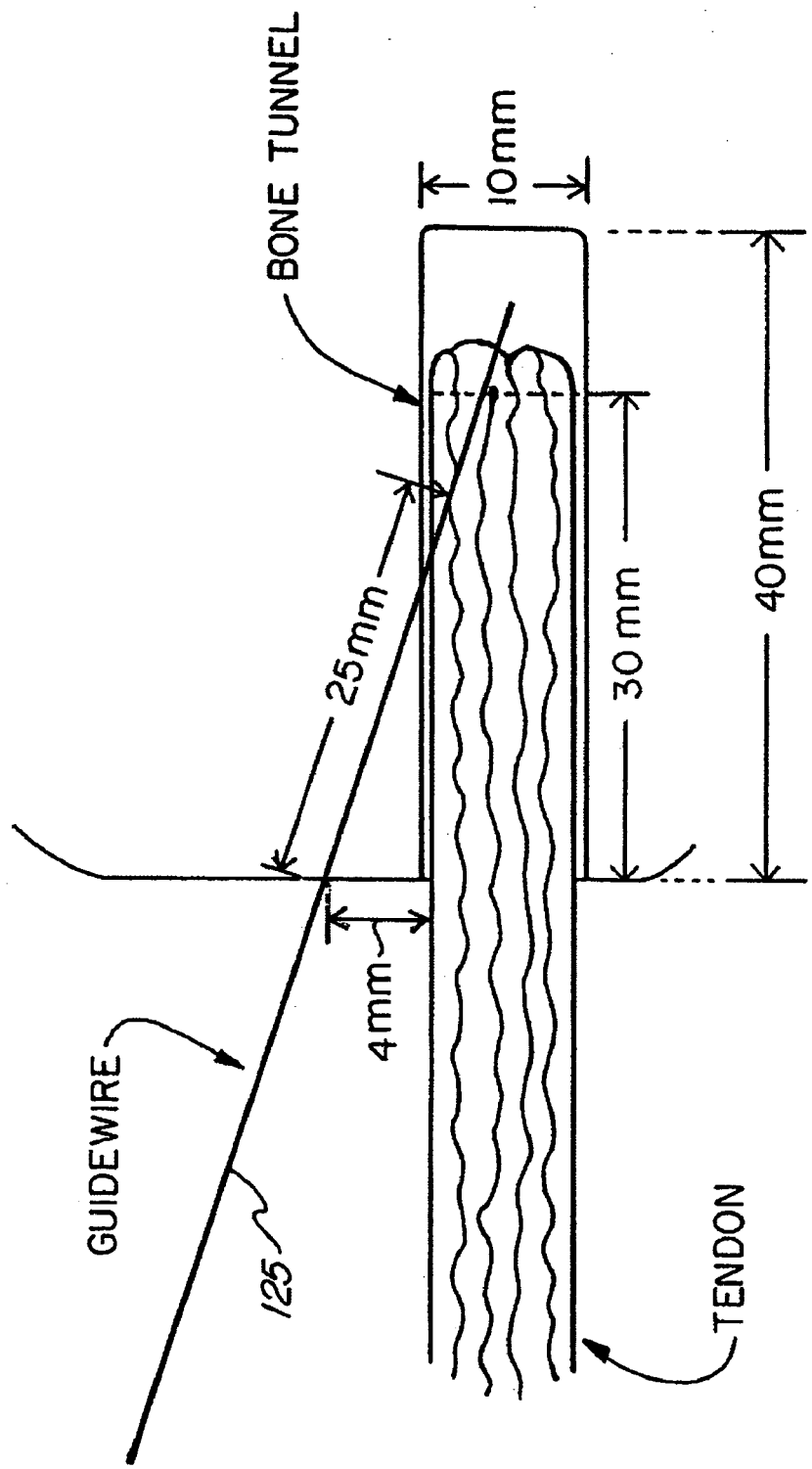
FIG. 6 is a schematic view showing a guidewire passed through the host bone and into the graft ligament by use of the guide of FIGS. 2, 3A and 3B.
Figure 7:
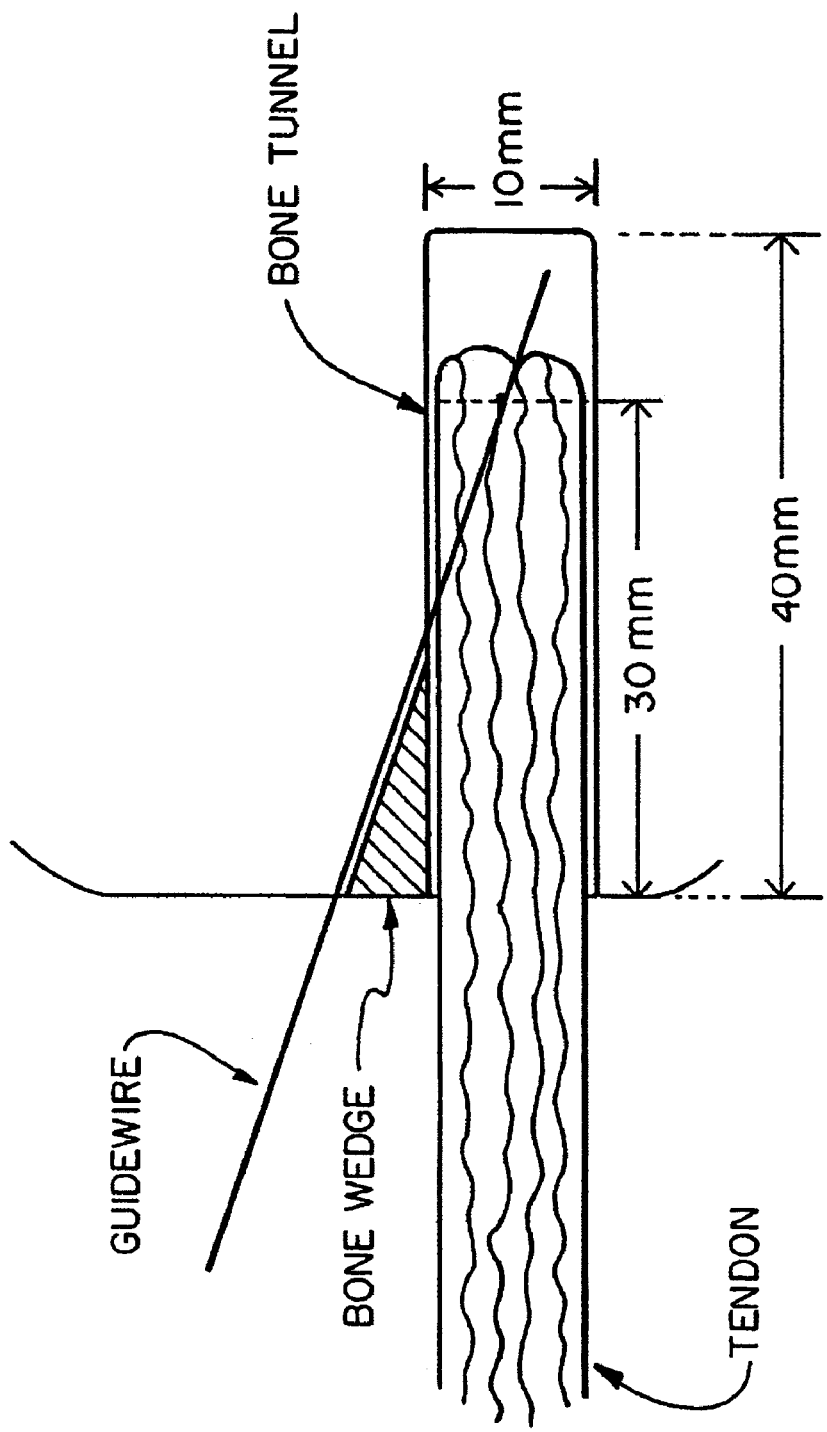
FIG. 7 is a schematic view showing the bone layer created by the osteotome that follows the angle predetermined in FIG. 6.

Preferably aimer 115 is constructed so that its bore 120 and slot 122 follow an axis that converges with the axis of foot 110, so that the osteotome following this line converges with the deep end of the tunnel, whereby to create a wedge-shaped layer of bone (FIGS. 6 and 7). The geometry of guide 100 also determines the thickness of the heel of the bone wedge. The exact optimal thickness of this wedge can vary, but is typically between about 3–6 mm (discussed in more detail below).

Figure 7B:
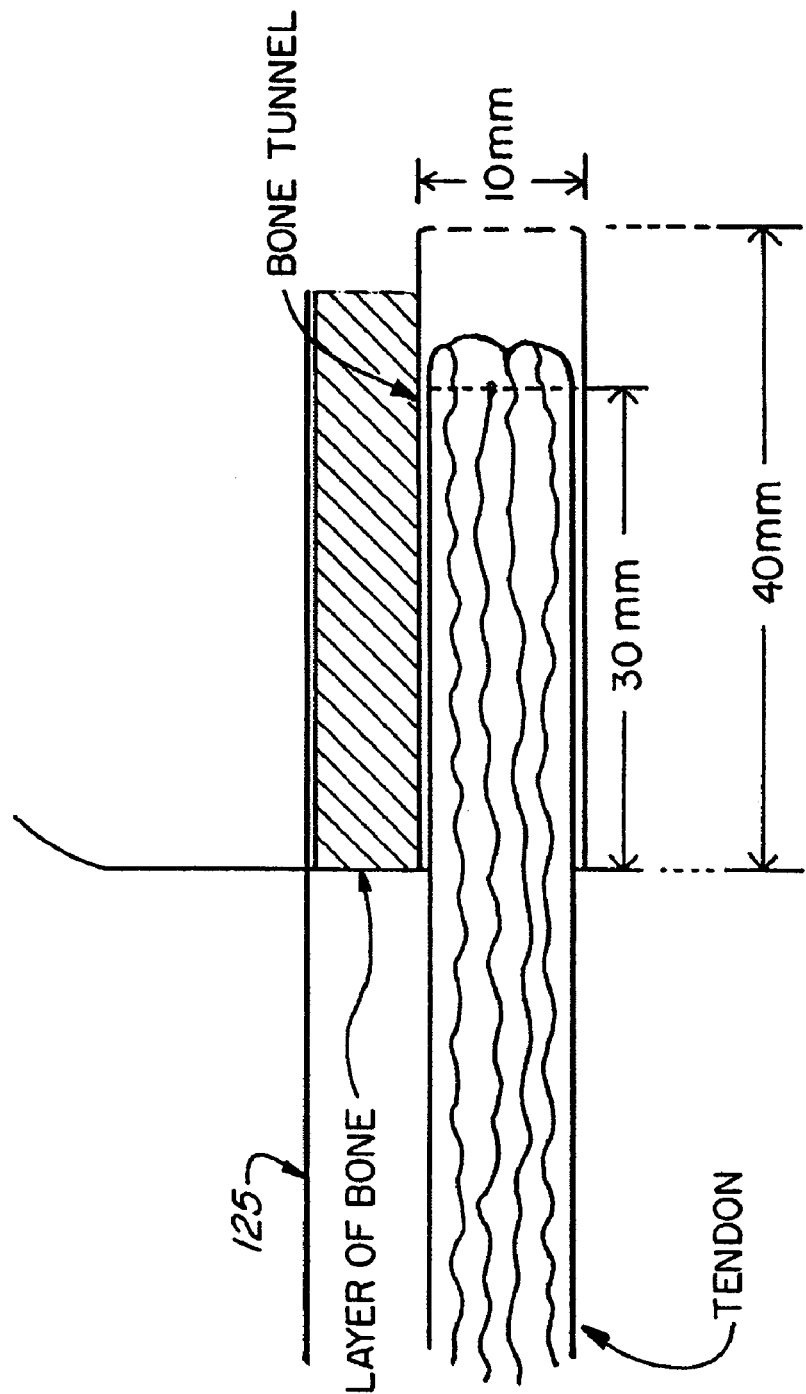

However, if desired, aimer 115 can be constructed so that its bore 120 and slot 122 follow an axis that is parallel to the axis of foot 110, so that the osteotome following this line will pass substantially parallel to the bone tunnel, whereby to create a relatively flat layer of bone (FIGS. 7A and 7B). The geometry of guide 100 will determine the thickness of the bone layer.

Figure 7C:
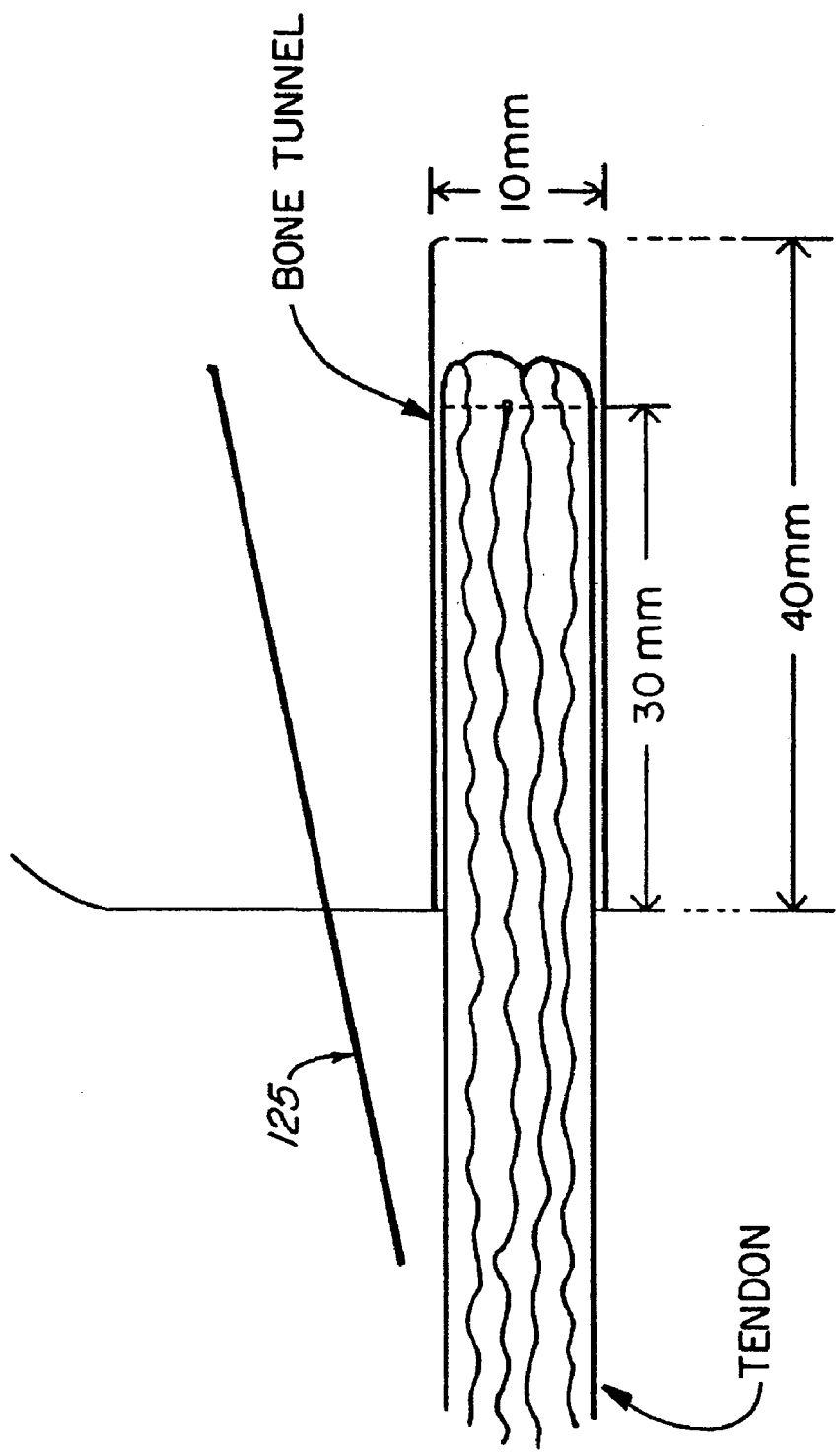
Figure 7D:
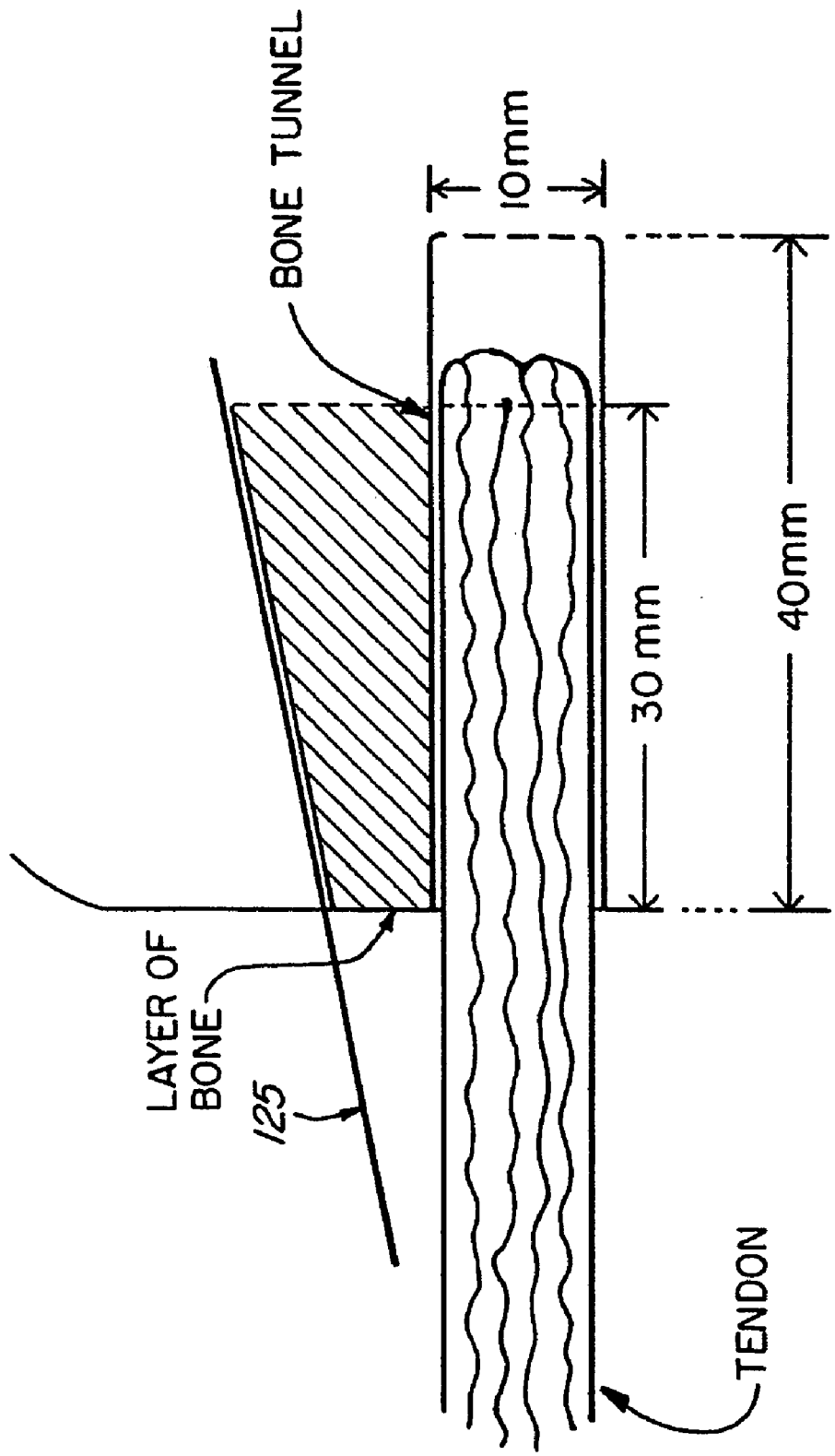

In still another form of the invention, aimer 115 may be constructed so that its bore 120 and slot 122 follow an axis that diverges from the axis of foot 110, so that the osteotome following this line will move away from the bone tunnel, whereby to create a distally-thickening layer of bone (FIGS. 7C and 7D).

Osteotome 200 is shown in FIGS. 4 and 5. Osteotome 200 generally comprises a handle 205 and a blade 210. When used with the cannulated system, lumen 215 extends through handle 205 and blade 210. Lumen 215 is sized to receive guidewire 125 therein, so that osteotome 200 can ride down guidewire 125 and create the desired layer of bone. As noted above, the shape of osteotome 200 and its angle of insertion are important elements of this technique. The osteotome 200 is preferably passed into the knee through the same anterior-medial knee portal normally used for screw insertion. This angle of insertion is preferably approximately 20–50 degrees different than the tunnel angle, depending on the degree of knee flexion. With the osteotome anterior to the tunnel, the converging angles of the osteotome and the bone tunnel create an intervening bone wedge layer terminating about 20–30 mm from the tunnel entrance as the osteotome penetrates into the tunnel itself.

The osteotome shape preferably includes several elements, and the particular instrument described here incorporates these elements. It should include a slim, narrow, pointed tip 220 to help guide the instrument and keep it in line with the tunnel. The osteotome should flare fairly steeply on its inferior surface 225 so as to aid in the initial compression of the bone wedge against the tendon. The overall width 230 (FIG. 5) of the osteotome should be slightly narrower than the bone tunnel diameter, creating a bone wedge just narrow enough to allow it to fit into the bone tunnel, with a slight break-away of each side of the wedge from the adjacent bone. Downwardly directed flanges 235 (FIG. 5) on each side of the osteotome aid in separating the intact wedge from the surrounding bone. The bone layer should be thin enough to allow easy compression into the tunnel but thick enough to help maintain the structural integrity of the bone wedge. The shape of the osteotome, at the level of the outer bone edge, is preferably arcuate, rounded or oval, creating an easy starting point for placement of the fixation device.

Figure 8:
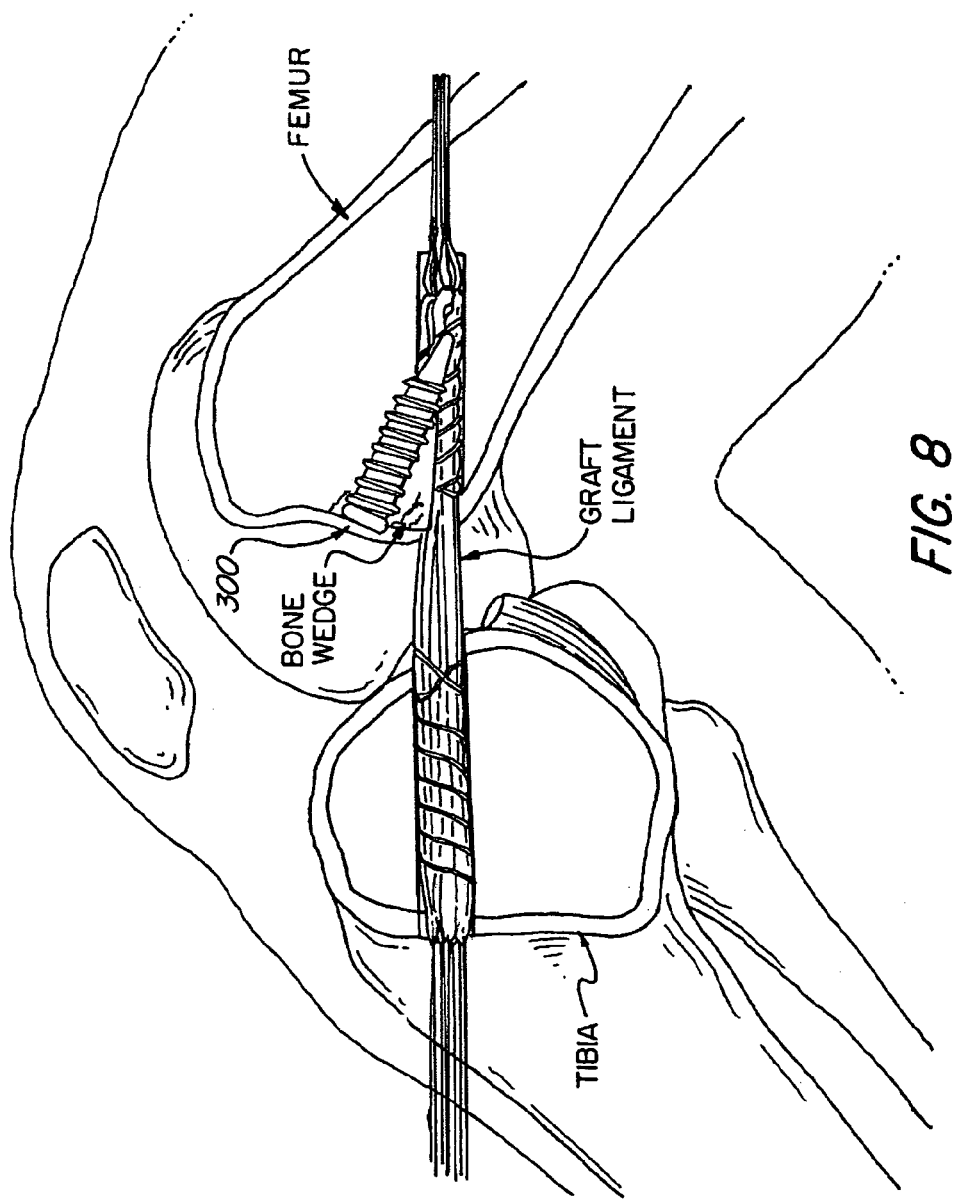
FIG. 8 is a schematic view showing an interference screw inserted above the intervening bone wedge, with compression and interference fixation of the tendon graft being established between the posterior bone tunnel wall and the anterior bone wedge.

During use, the ligament is first placed in the bone tunnel (FIG. 1). If using guide 100, the guide is inserted into the tunnel so that its foot 110 (FIGS. 2 and 3A) extends between the outer surface of the ligament and the deep wall of the bone tunnel. Then the guidewire 125 is run down aimer 115 (FIGS. 2 and 3B) and into the bone. The guidewire 125 is preferably advanced until it passes into the end of the tendon graft. Guide 100 is then withdrawn, leaving the guidewire 125 in place (FIG. 6). Then osteotome 200 is advanced over the guidewire, into the bone and then withdrawn. Withdrawal of the osteotome leaves behind a small "tunnel above the tunnel", with an intervening wedge shaped layer of bone (FIG. 7). The bone wedge is depressed inferiorly, into the bone tunnel, with slight micro-fracturing of the bone layer edges, permitting displacement of the wedge. The interference fixation device (e.g., a traditional interference screw or a specially designed interference fixation device 300 such as shown in FIG. 8) is then advanced above the wedge of bone, with or without use of a guidewire, and through the osteotomy site, and preferably directly into the end portion of the tendon-graft substance. See FIG. 8.

One of the currently commercially available interference screws may be used to provide fixation. Alternatively, a wedge-shaped element, or a frusto-conical pin, or some other form of object, preferably with ribs or ridges so as to retard withdrawal, may be used to force the formed layer of bone away from the host bone and thereby effect fixation. However, creation of a new screw shape and configuration specific for this technique represents a new device that should help improve tendon-graft fixation strength. Optimal screw length can be estimated by the use of measurement markings etched directly on the osteotome or by use of a depth gauge, if desired. Lengthening the tip of the screw and making the tip relatively "sharper" than the currently blunt-tipped screws creates a pin-like configuration that allows the tip of the screw to penetrate the tendon substance at the osteotomy/bone tunnel interface, providing some degree of tendon transfixation and thereby improving pullout strength. Altering the pitch and lead of the screw may also be beneficial, as the screw will be primarily interfacing with bone, as opposed to half bone, half tendon as is normally the situation. Also, a screw that has a degree of taper may also work better; the increased diameter at the butt end of the screw may increase compression of the bone wedge into the tendon (FIG. 8).

Figure 9:
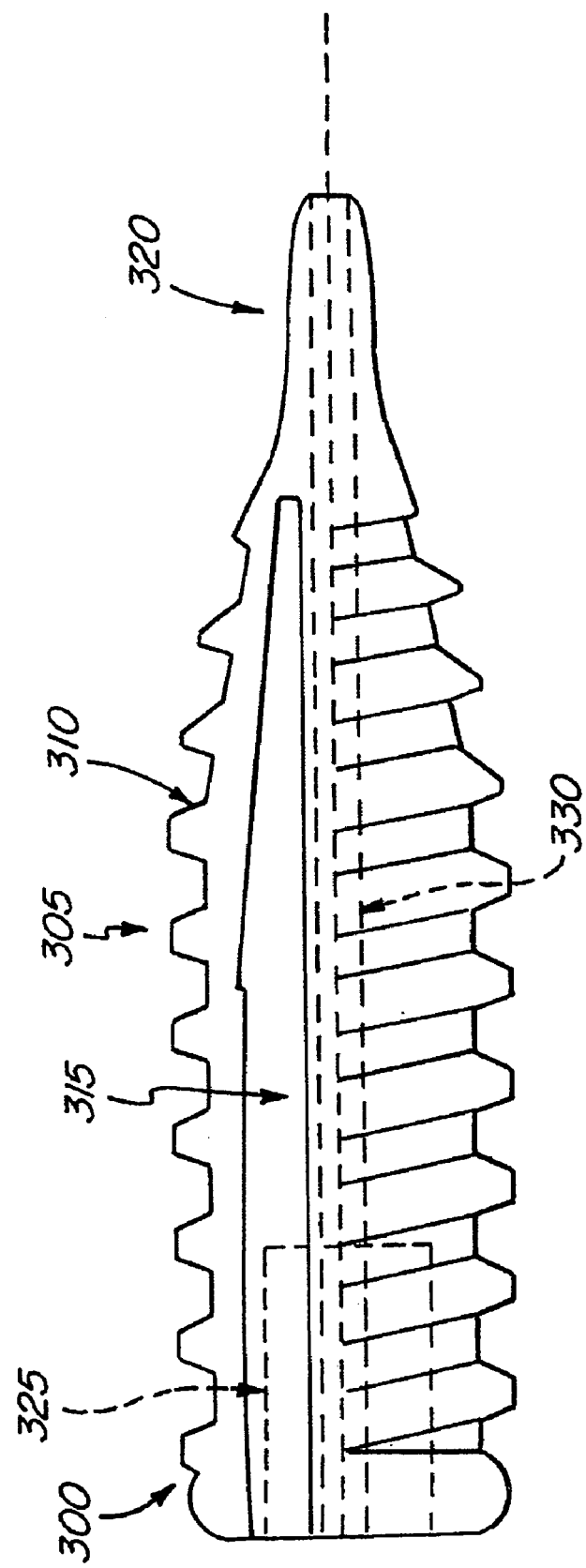
FIG. 9 is a schematic view showing a novel interference fixation device that can be utilized with the present invention.

Thus, for example, in FIG. 9 there is shown a novel interference screw 300 which comprises one preferred form of interference fixation device. Screw 300 generally comprises a body 305 including screw threads 310. A cutting flute 315 may also be provided. An elongated leading tip 320 is disposed at the distal end of body 305. Tip 320 is preferably sufficiently sharp to be able to transfix a ligament by passing at least partially therethrough. Screw 300 also includes a non-circular (e.g., hexagonal) recess 325 at its proximal end for receiving a driver (not shown) whereby the interference screw may be turned. If desired, screw 300 may be cannulated with a lumen 330 so that it may be deployed over a guidewire or the like.

Figure 10:
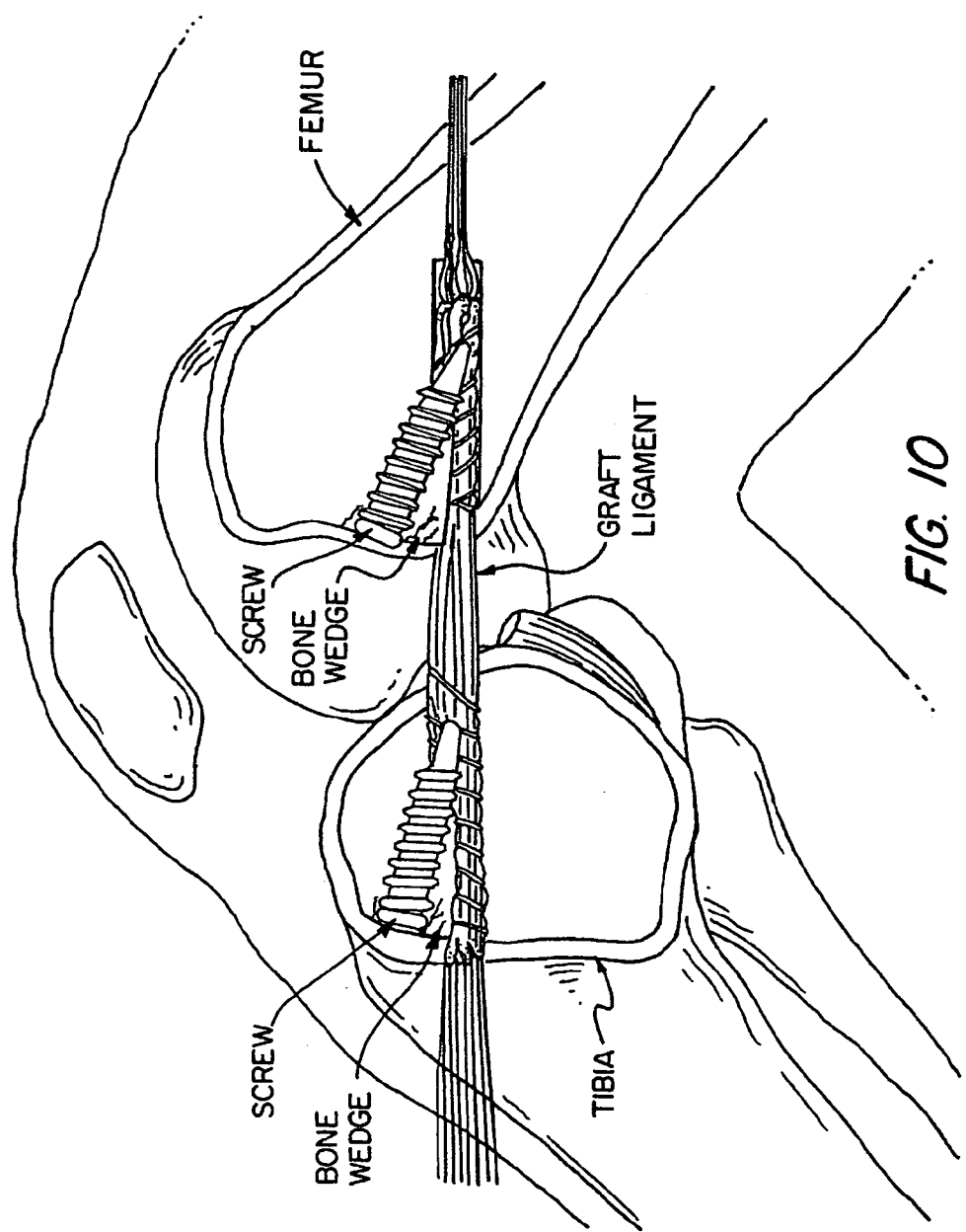
FIG. 10 is a schematic view showing the invention being used on both the femoral and tibial sides of an ACL reconstruction.
Figure 11:
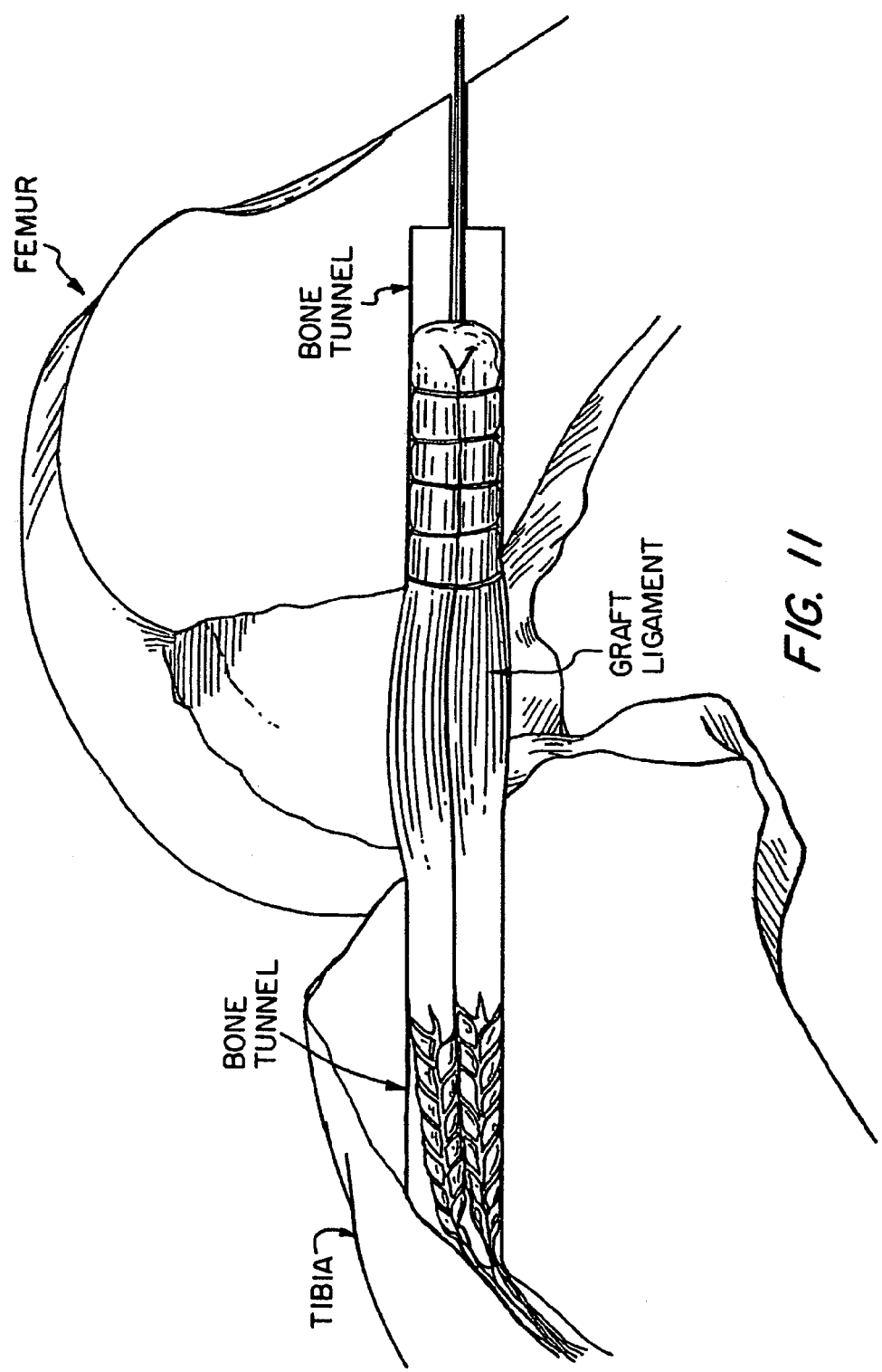
FIGS. 11–25 show further aspects of the present invention in the context of an ACL reconstruction.
Figure 12:
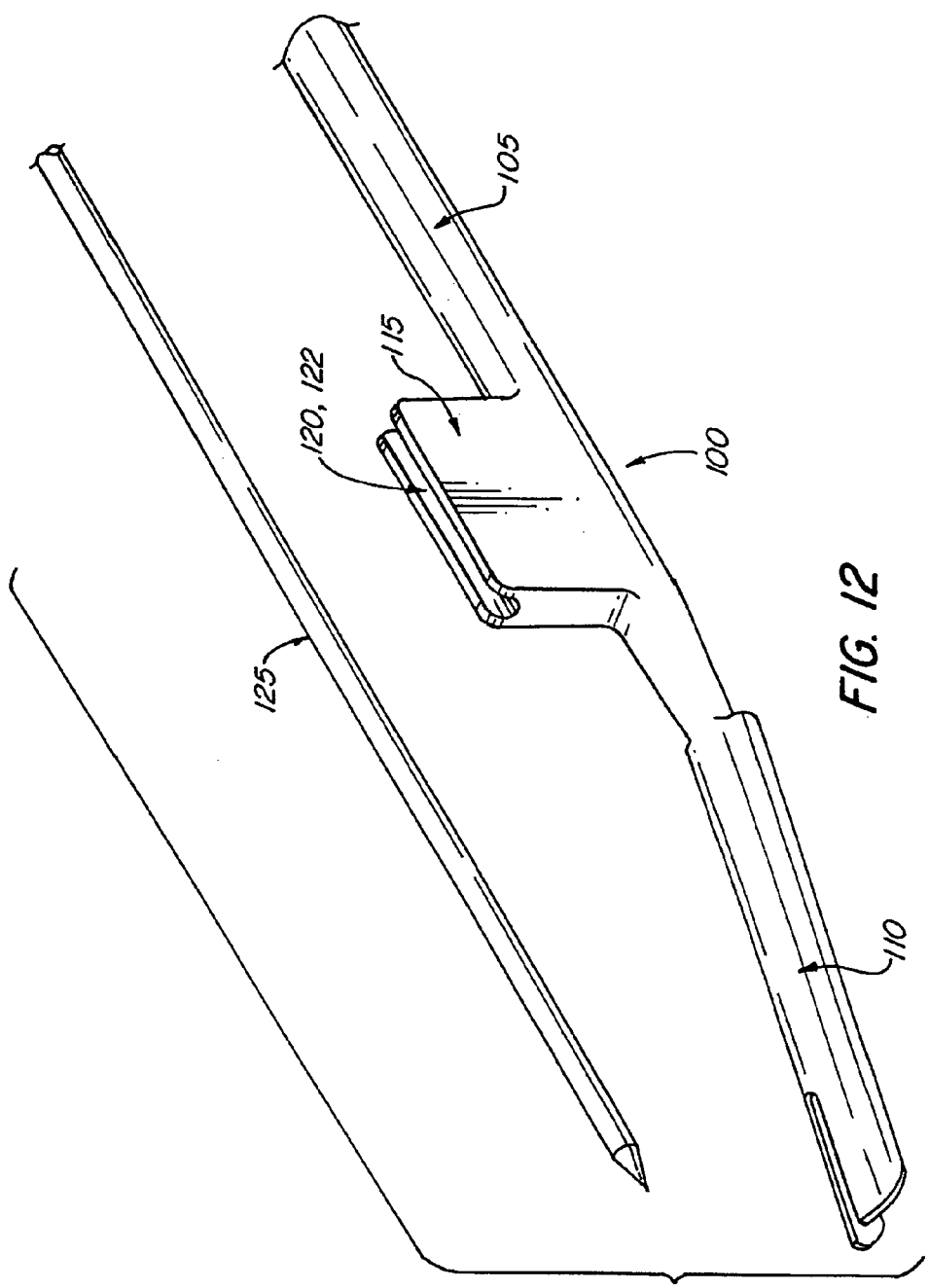
Figure 13:
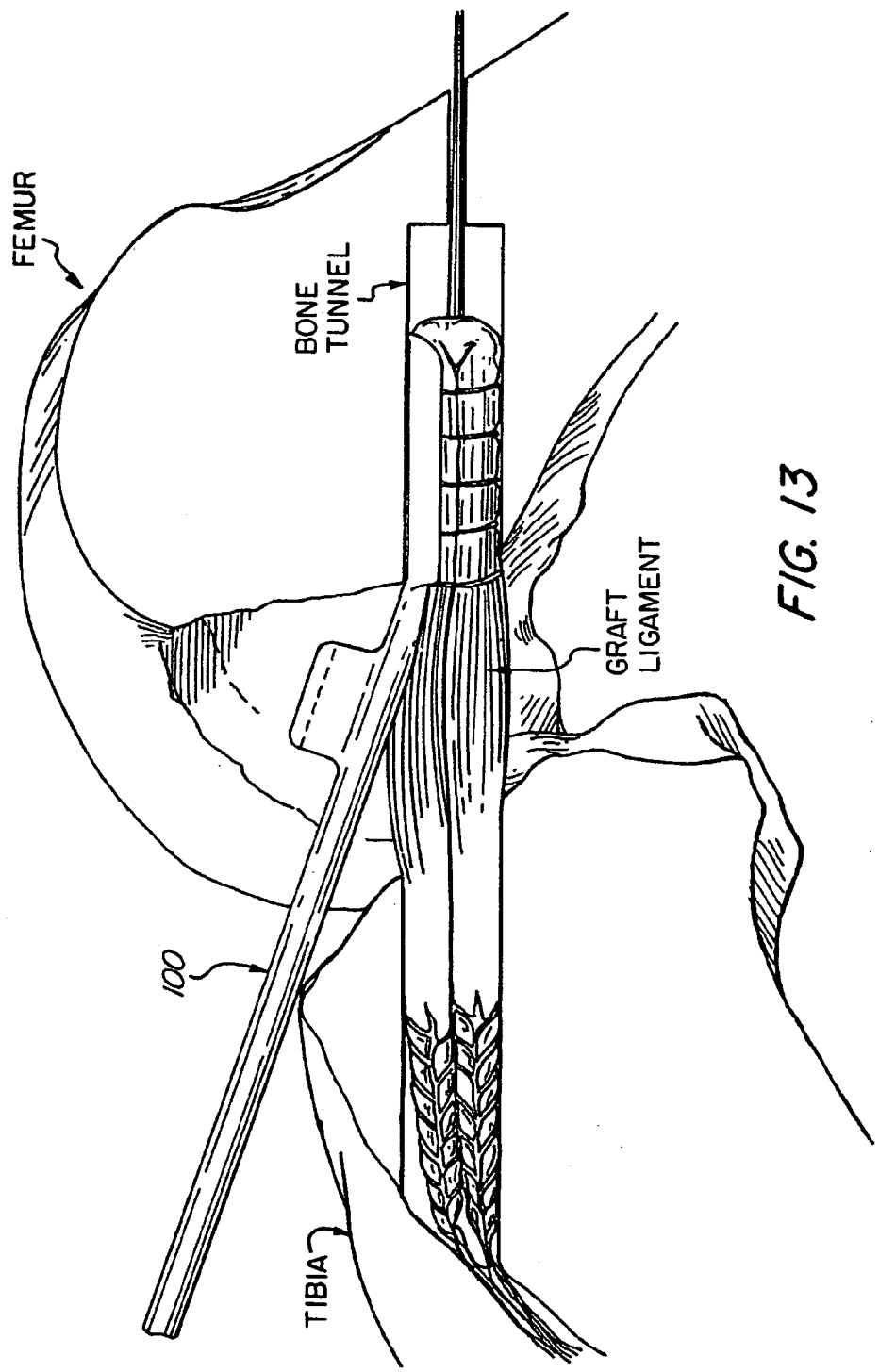
Figure 14:
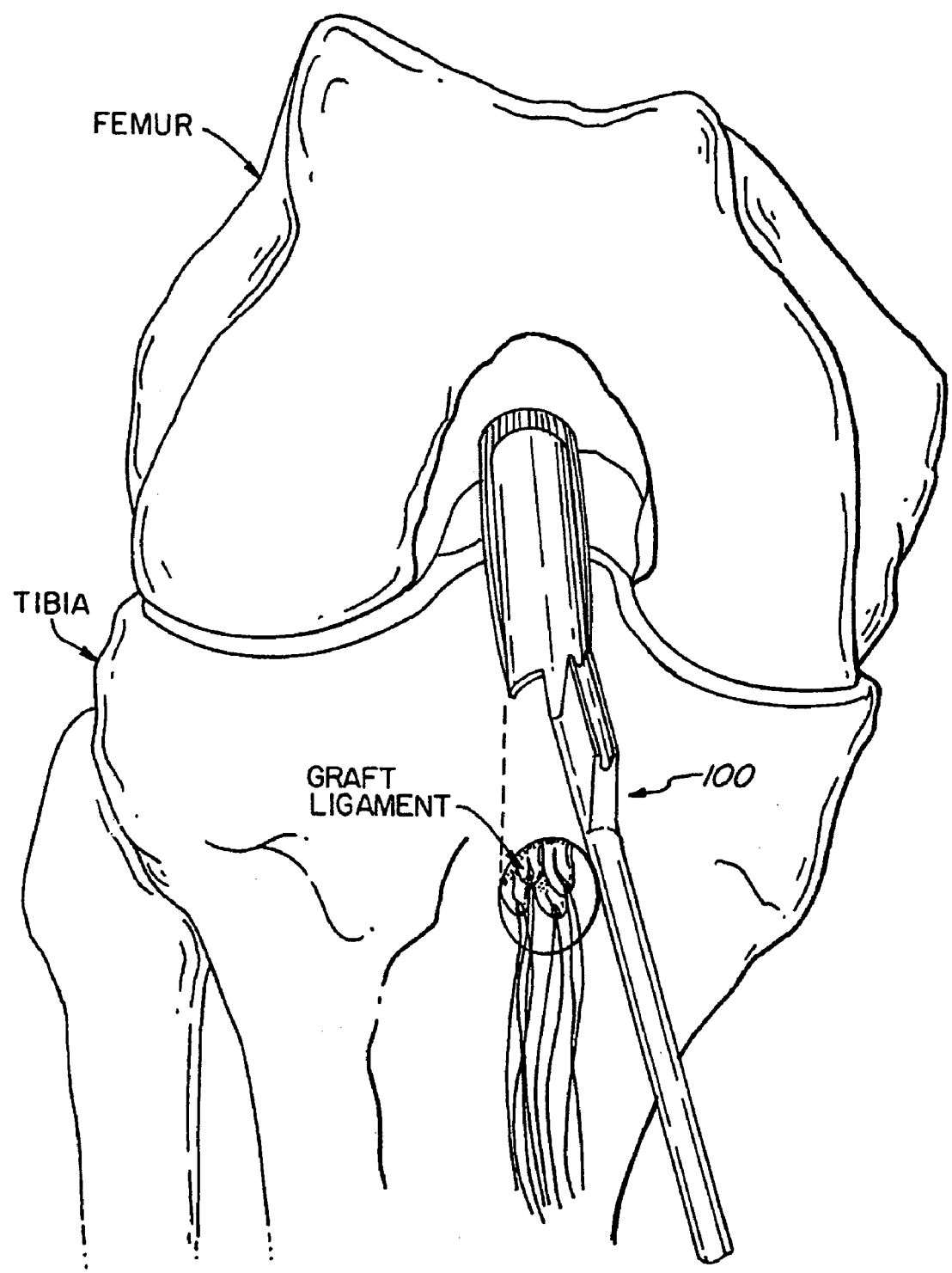
Figure 15:
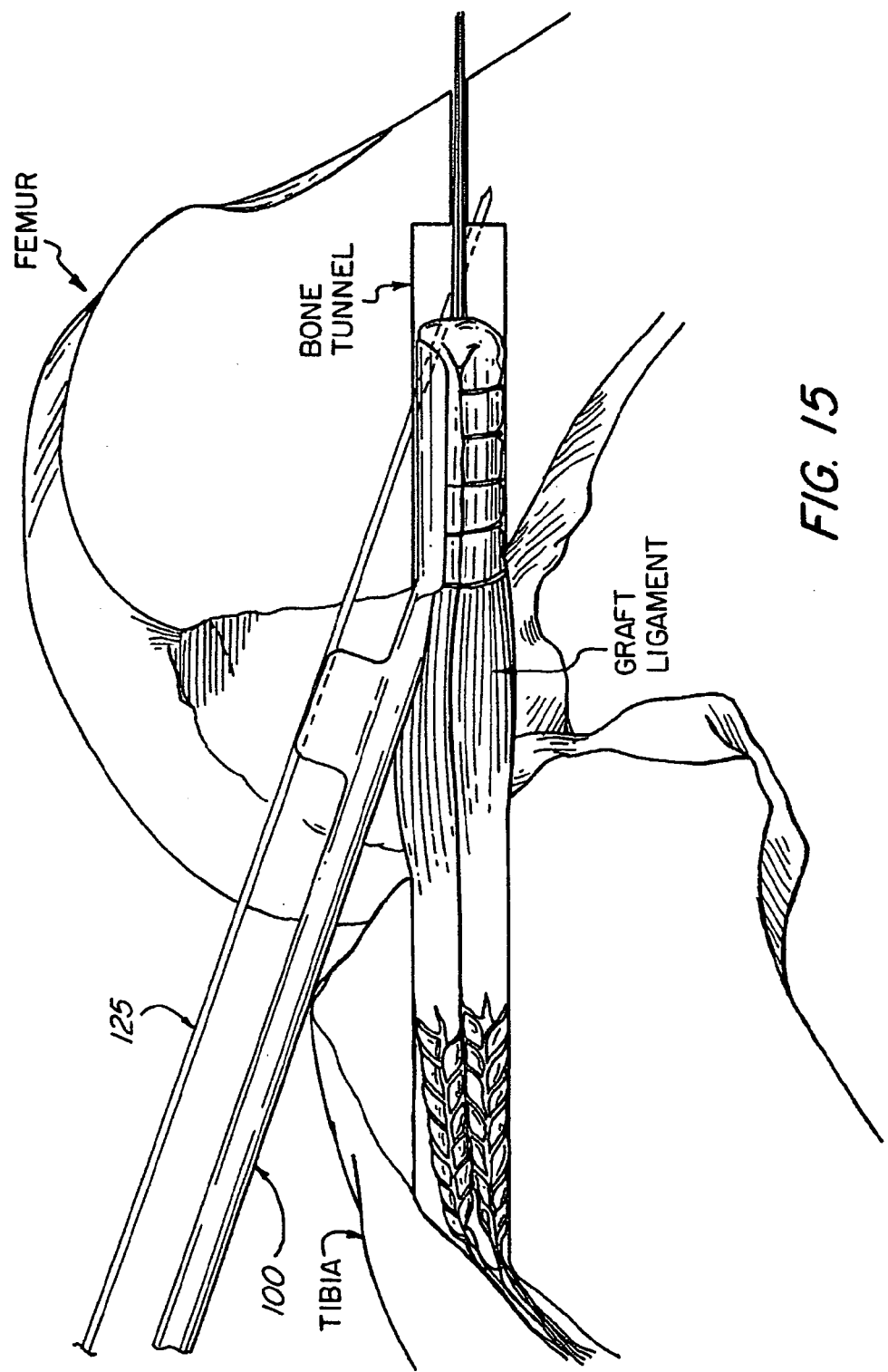
Figure 16:
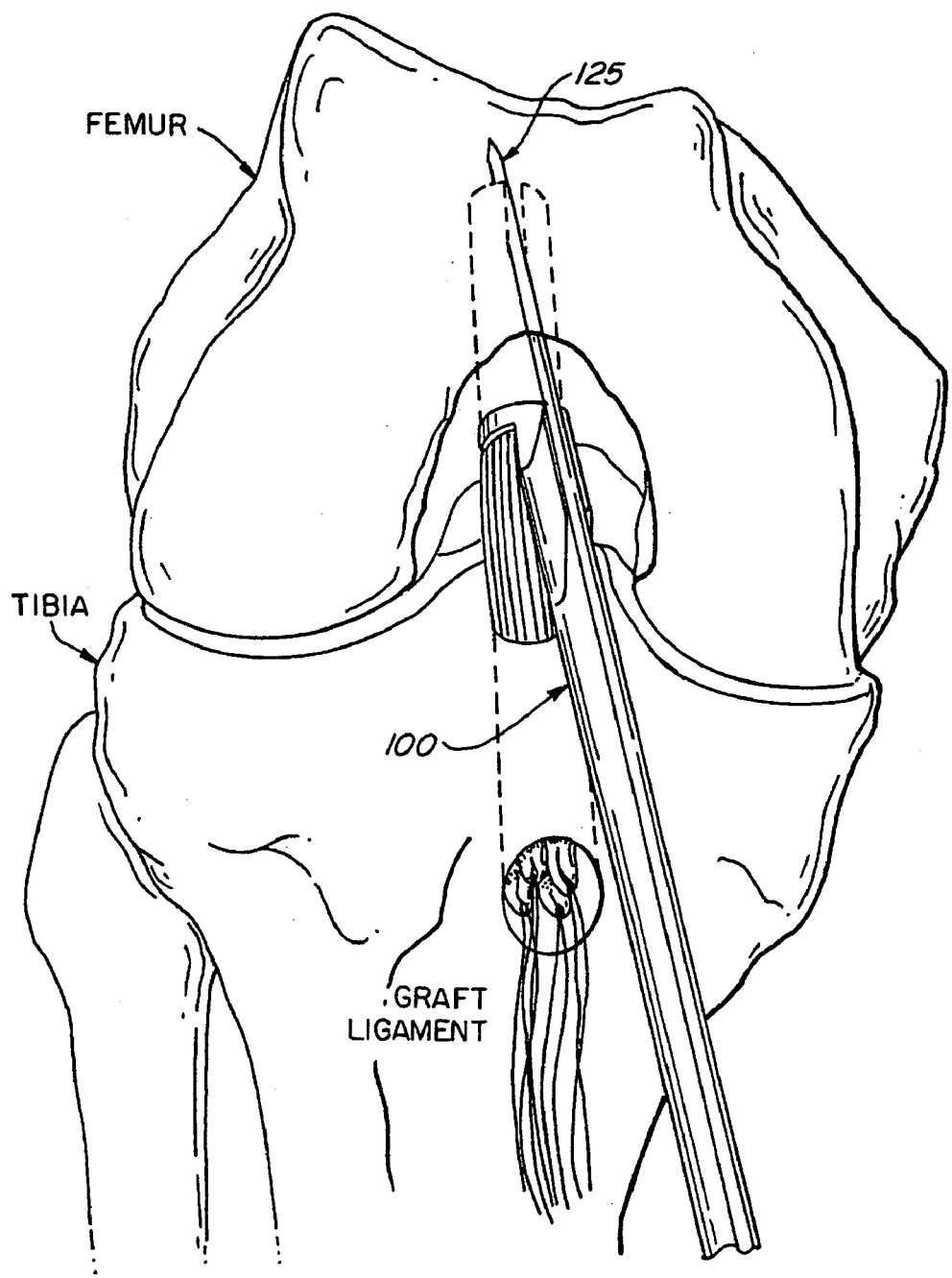
Figure 17:
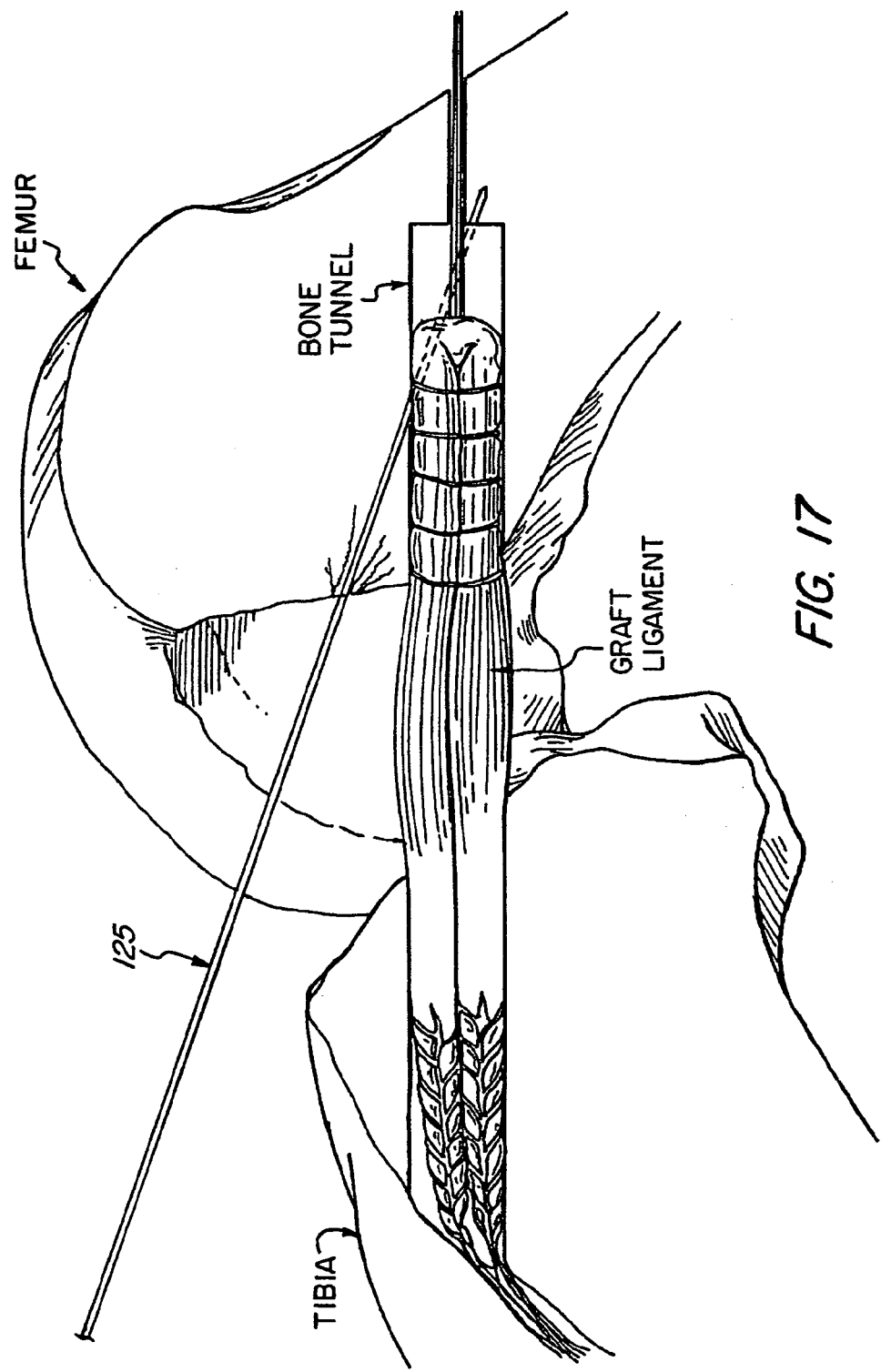
Figure 18:
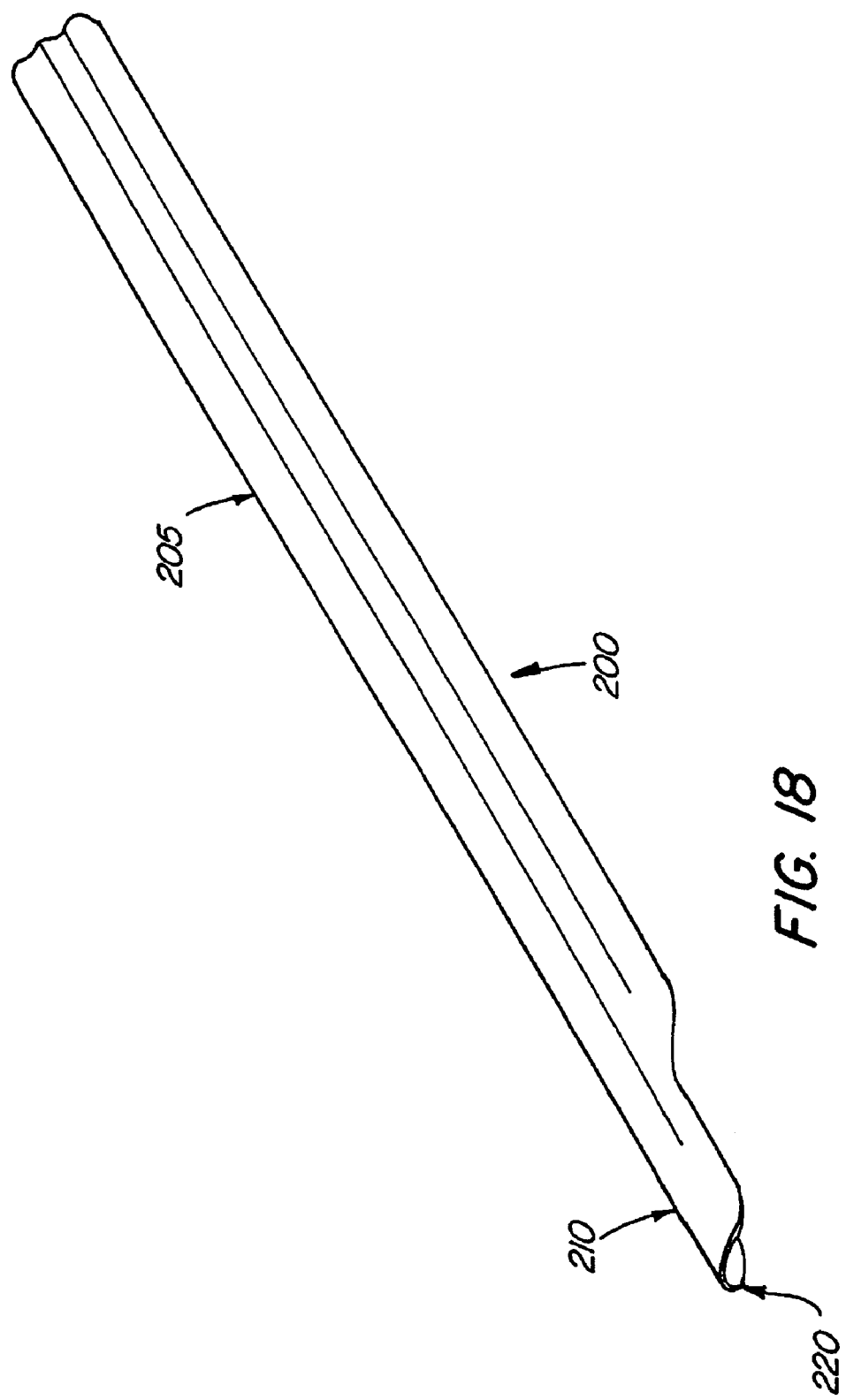
Figure 19:
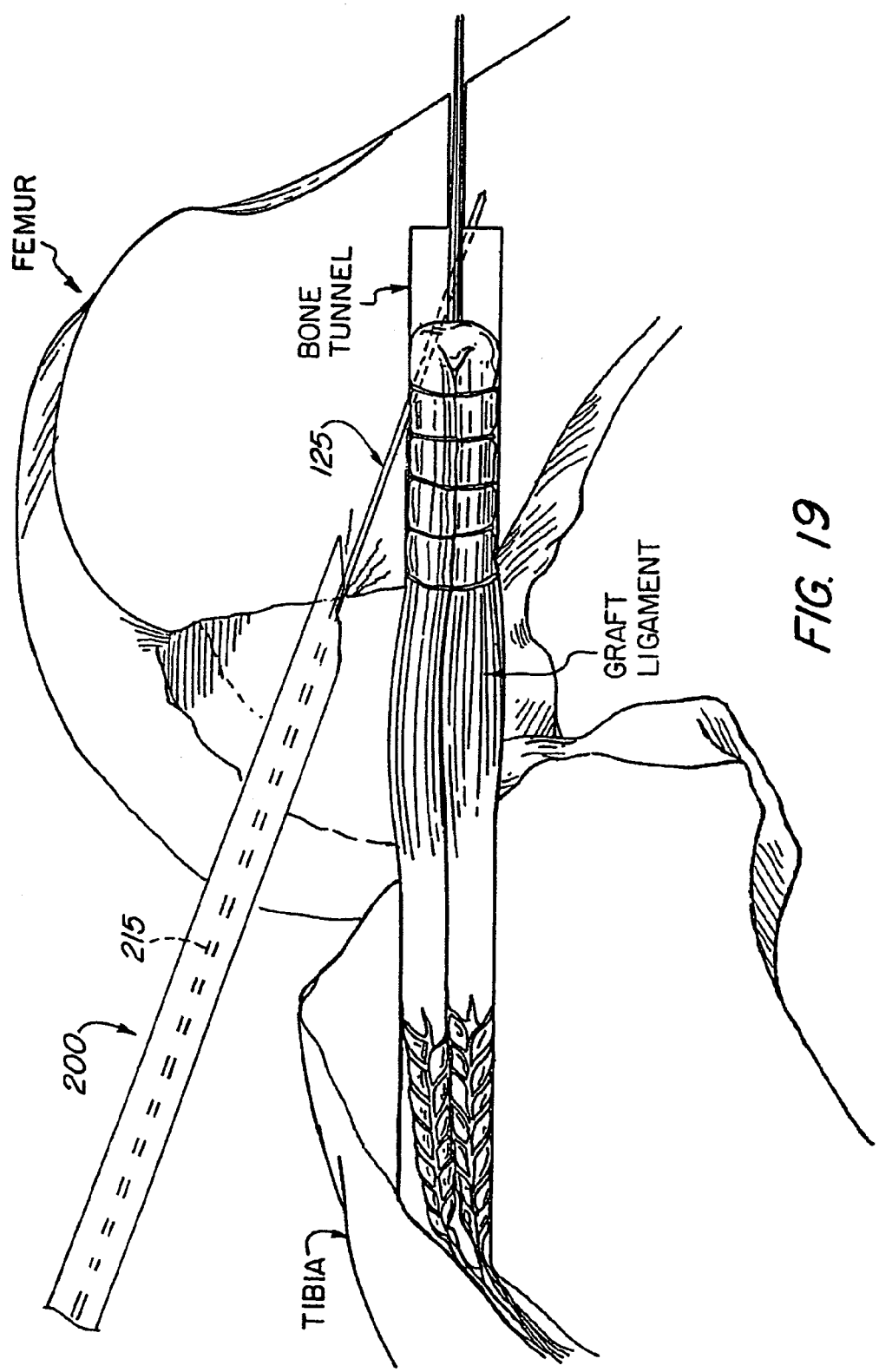
Figure 20:
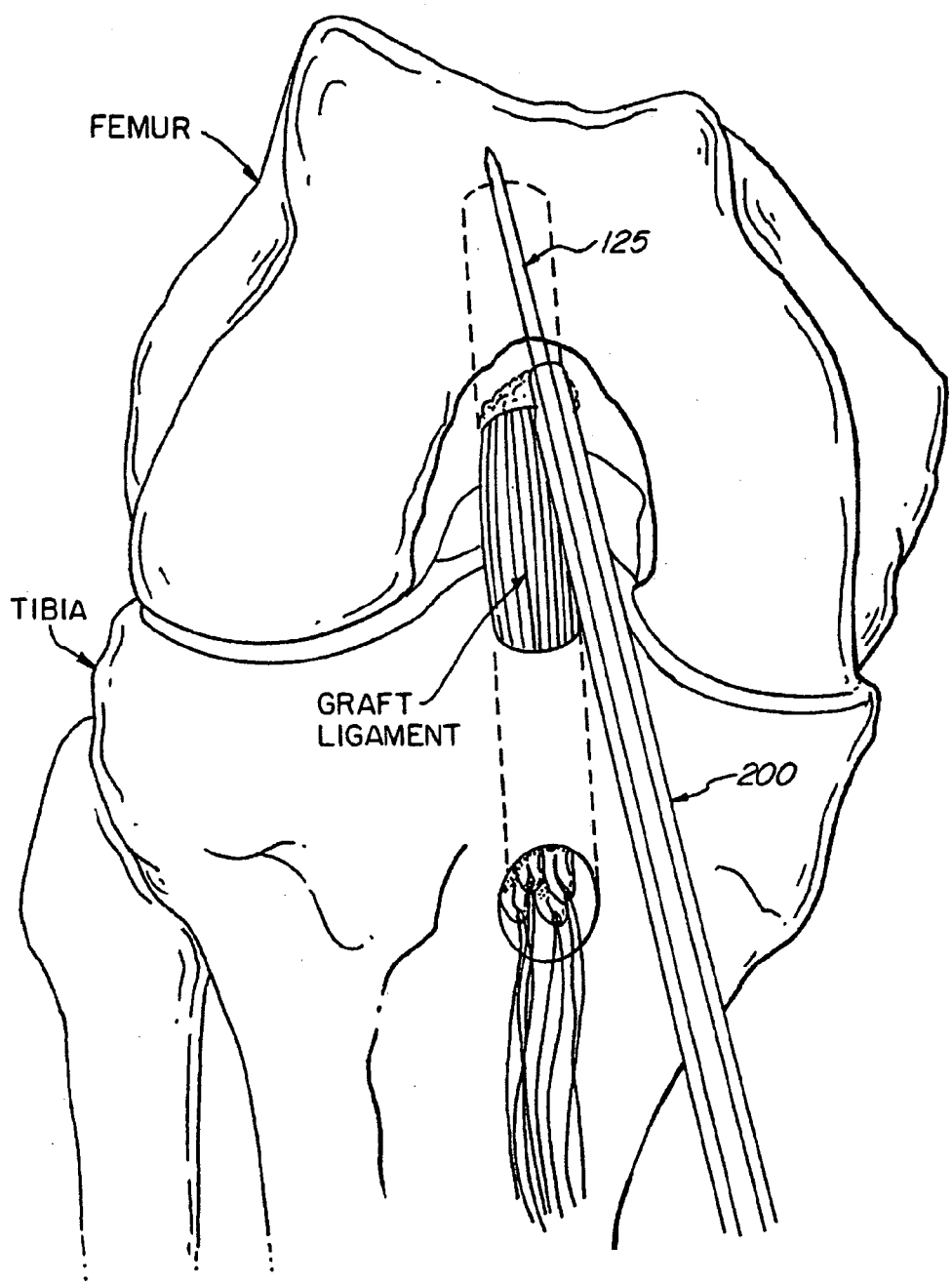
Figure 21:
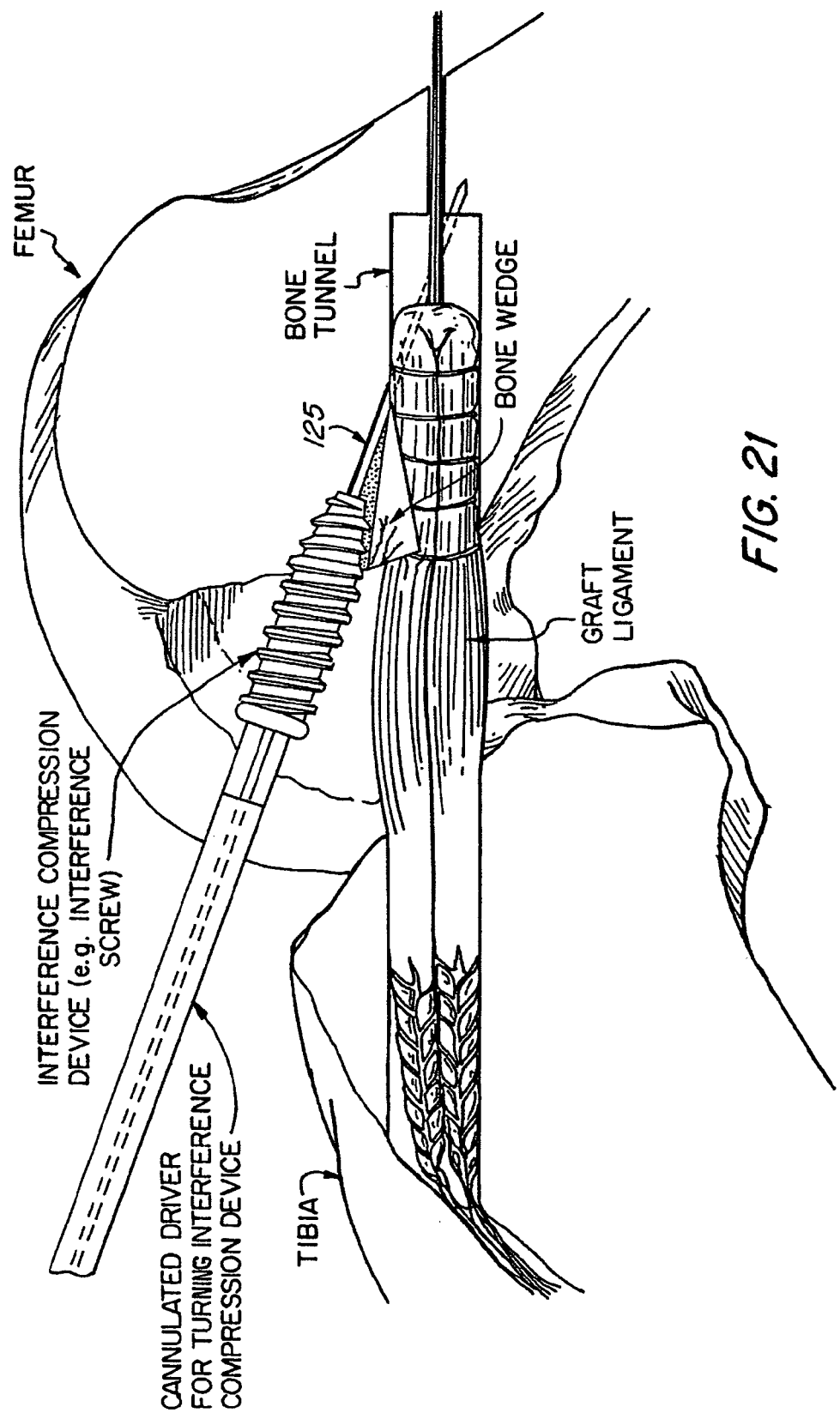
Figure 22:
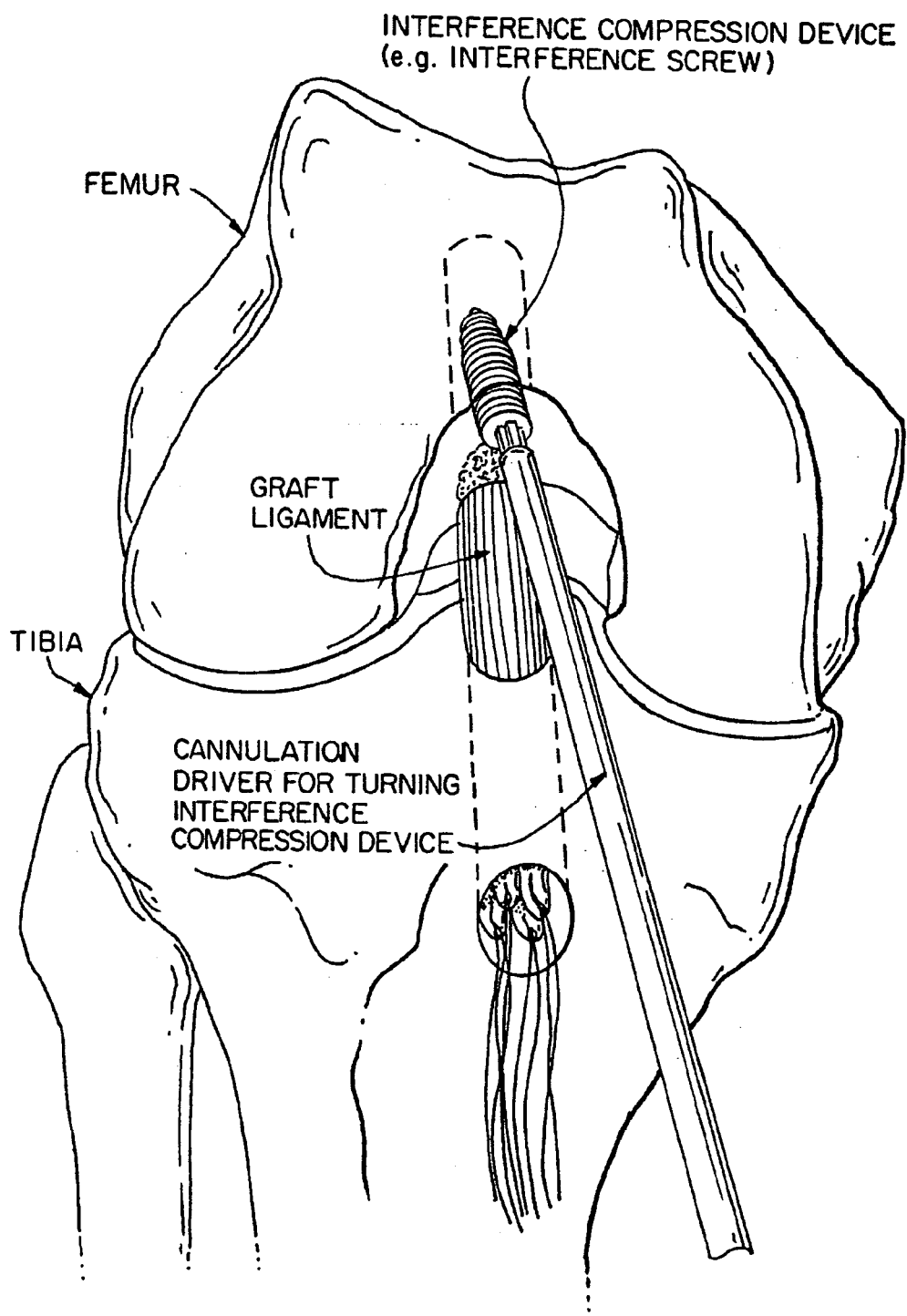
Figure 23:
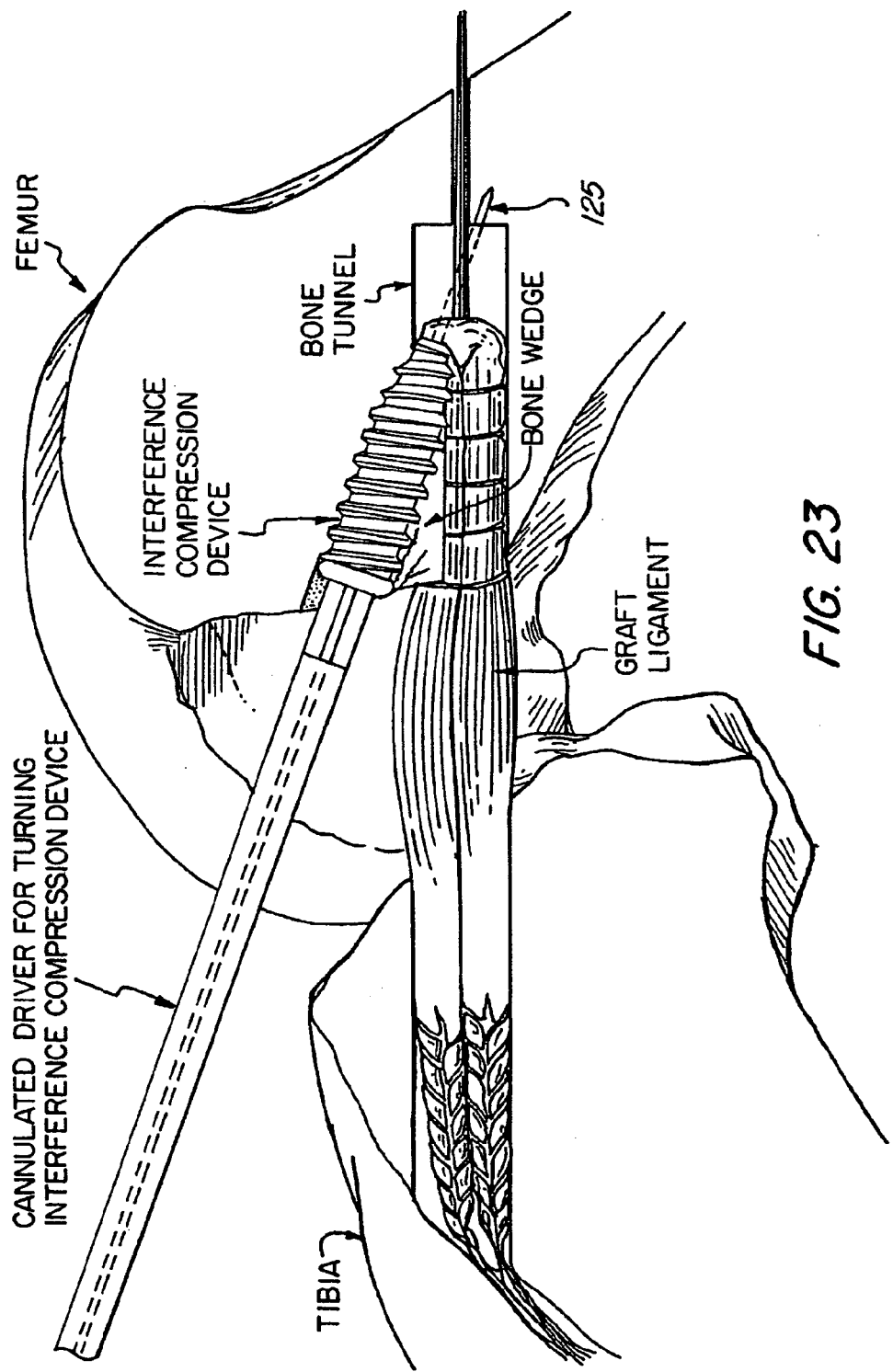
Figure 24:
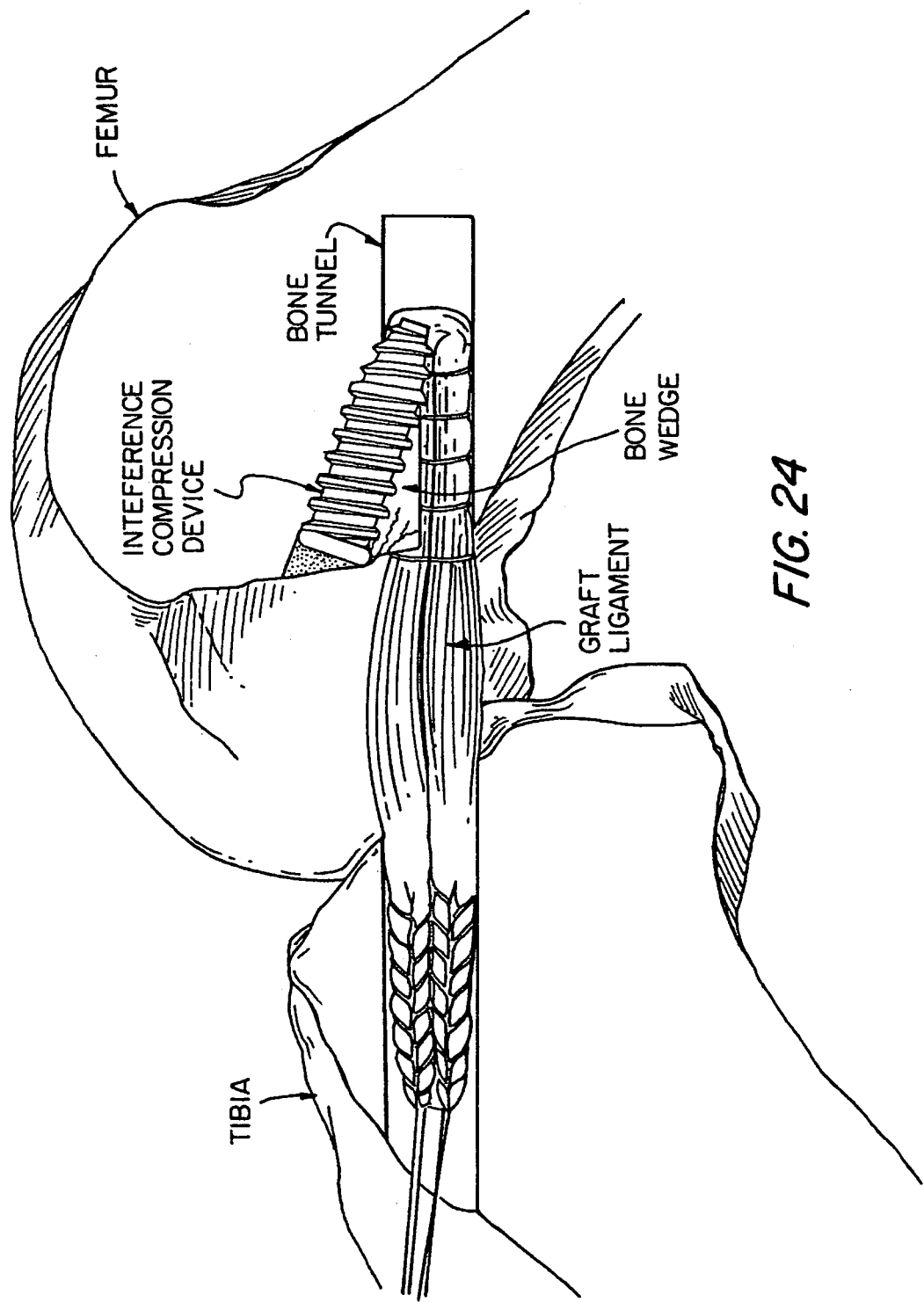
Figure 25:
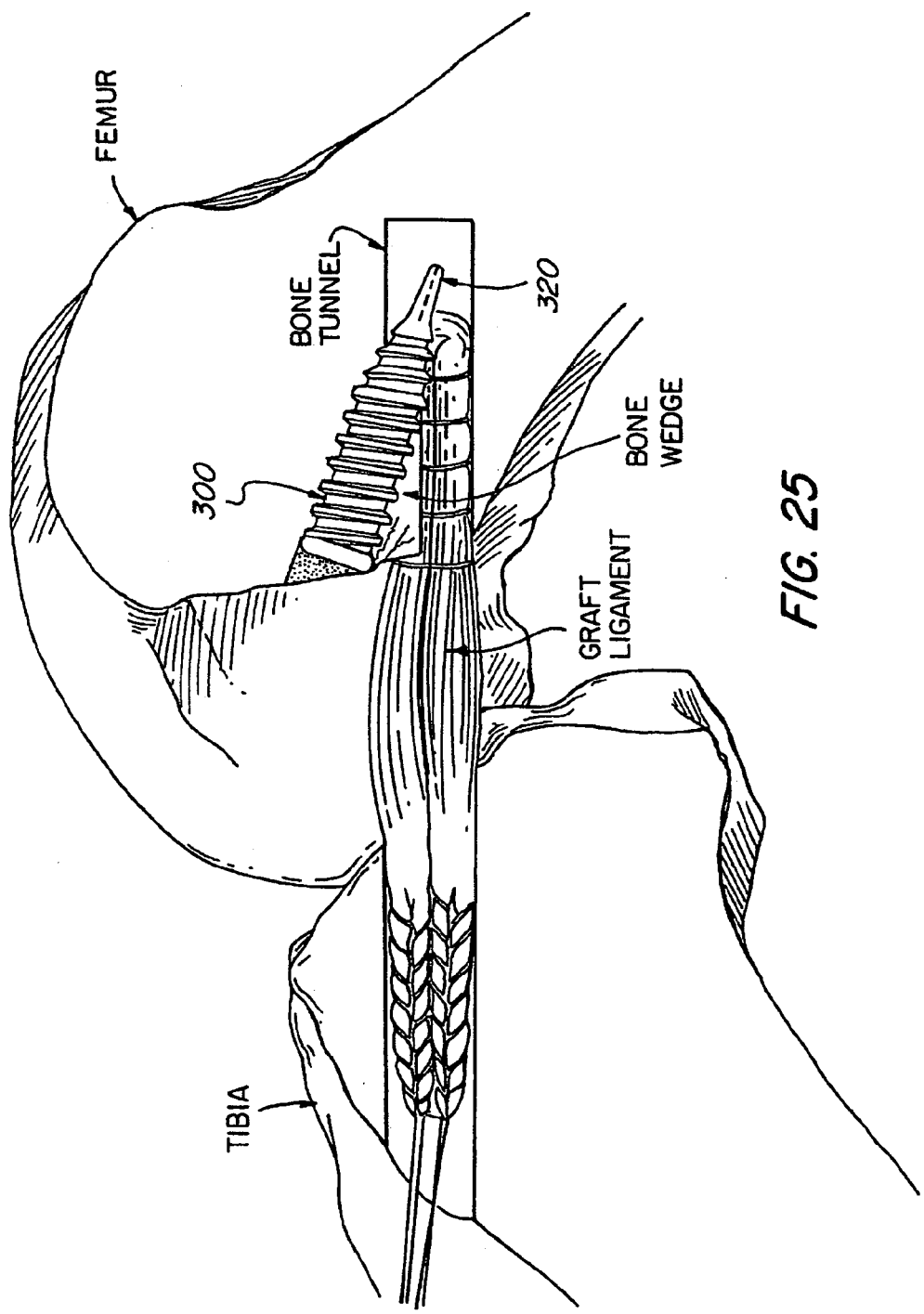

As noted above, the foregoing description of the femoral side of an ACL reconstruction is intended to be merely one example of the multiple uses of the present invention. Thus, for example, the invention may also be used on the tibial side of an ACL reconstruction (see, for example, FIG. 10, which shows the invention being used on both the femoral and tibial sides of an ACL reconstruction). Or the invention may be used in other types of ligament reconstruction.

It is also possible to form the desired layer of bone with a non-cannulated osteotome. More particularly, guide 100 can be used to form a guide hole into the bone with its guide pin or guidewire 125, whereupon the guide 100 and guide pin or guidewire 125 are removed, leaving a guide hole in the bone. Then an osteotome 200A (FIGS. 10A–10C) is used to form the desired layer of bone. Osteotome 200A is preferably substantially identical to the osteotome 200 described above, except that its lumen 215 is replaced by a guide tip 215A. During formation of the desired bone layer, guide tip 215A is advanced into the guide hole in the bone, whereby to regulate the path and/or depth of penetration of the osteotome.

FIGS. 11–25 show further aspects of the present invention in the context of an ACL reconstruction.

If desired, the techniques of the present invention may be used alone, as the sole manner of fixing the graft ligament in the bone tunnel. Alternatively, the present invention may be used in addition to another type of fixation system, e.g., an ENDOBUTTON™ system or cross-pinning, etc.

There are several significant advantages to using this fixation system over the conventional systems currently in use. First, the tendon is still held in place by tight interference compression, but it is now surrounded by native bone. Compression on each side of the graft by cancellous bone significantly enhances circumferential bone ingrowth potential. The bone wedge has not been displaced significantly, thus allowing rapid bony healing circumferentially around the tendon graft. With the deep end of the screw at least partially imbedded into the deep portion of the tendon, any traction on the graft will likely have a "deadmanlike" pull on the screw tip, wedging the butt end of the screw into the overlying bone as tension on the graft pulls on the screw tip, thereby enhancing fixation. Also, any fixation benefits derived from the presence of a bone block or the use of fixation-augmentation devices attached to the end of the tendon, such as the ENDO-PEARL™ or similar devices, would be enhanced. The displacement of the graft attached to any of these devices or bone blocks would be inhibited by the presence of the bone wedge between the device or bone block and the tunnel outlet. Also, exclusion of synovial fluid from the bone tunnel, an ingrowth-enhancing advantage of interference fixation, is maintained.

A key but often under-appreciated element of the high pullout values in some of the more recent interference fixation studies is that the high values are usually very technique dependent. An interference screw that diverges during insertion can negate the benefits of even the best tunnel and graft preparation. The precise positioning of the screw in the bone tunnel is crucial. However, this is not always easy to control. Also, spinning of the tendon graft during insertion of the screw is a well-documented problem that is difficult to control once it has begun. This "tendon spin" can damage the graft and result in impingement and less than ideal graft positioning, possibly affecting the clinical results. One of the obvious immediate benefits of this new fixation approach is that tendon spin is completely eliminated. The fixation screw device turns against bone on all sides, preventing any occurrence of tendon spinning during insertion of the device. Screw location and placement is more controllable with the new system described here, making the results more predictable.

What is claimed is:

1. A method for reconstructing a ligament, the method comprising:
   creating a bone tunnel within a host bone, the bone tunnel having a proximal end and a distal end, and defining a central axis extending from the proximal end to the distal end;
   incompletely breaking away a wedge-shaped layer of bone from the rigid portion of the host bone surrounding the bone tunnel so as to hinge inwardly toward the central axis of the bone tunnel to create an intervening layer of bone between the central axis of the bone tunnel and a rigid portion of the host bone, the intervening layer having a first side and a second side in opposition to one another, the first side of the intervening layer facing toward the central axis of the bone tunnel and the second side of the intervening layer facing toward the rigid portion of the host bone; and
   compressing the intervening layer of bone against a graft ligament positioned within the bone tunnel.

2. The method of claim 1 wherein the graft ligament is positioned in the bone tunnel prior to the step of creating the intervening layer of bone between the central axis of the tunnel and the rigid portion of the host bone.

3. The method of claim 1 wherein the graft ligament is positioned in the bone tunnel subsequent to the step of creating the intervening layer of bone between the central axis of the bone tunnel and the rigid portion of the bone.

4. The method of claim 1 wherein the intervening layer of bone comprises an intact portion of bone divided away from the host bone.

5. The method of claim 1 wherein incompletely breaking away the wedge-shaped layer of bone from the rigid portion of the host bone maintains bone-to-bone opposition between the wedge-shaped layer and the rigid portion of host bone.

6. The method of claim 1 wherein the step of compressing the intervening layer of bone against the graft ligament positioned within the bone tunnel comprises positioning an interference compression device between the intervening layer of bone and the rigid portion of the host bone.

7. The method of claim 6 wherein the interference compression device is positioned between the intervening layer of bone and the rigid portion of the host bone so as to compress a substantial portion of the graft ligament between the intervening layer of bone and the rigid portion of the host bone and so as to contact a substantial portion of a perimeter of the graft ligament with the intervening layer of bone and the rigid portion of the host bone.

8. A method according to claim 6 wherein said interference compression device comprises an interference screw.

9. A method according to claim 1 wherein said graft ligament is additionally supported within said bone tunnel with an additional fixation device.

10. A method according to claim 9 wherein said additional fixation device comprises an ENDOBUTTON™.

11. A method according to claim 9 wherein said additional fixation device comprises a cross-pin.

12. A method for reconstructing a ligament, the method comprising:
   creating a bone tunnel within a host bone, the bone tunnel having a proximal end and a distal end, and defining a longitudinal central axis extending from the proximal end to the distal end;
   incompletely breaking away a wedge-shaped layer of bone from the rigid portion of the host bone surrounding the bone tunnel so as to hinge inwardly toward the central axis of the bone tunnel to create an intervening layer of bone between the central axis of the bone tunnel and a rigid portion of the host bone, the intervening layer having a first longitudinal side and a second longitudinal side in opposition to one another, the first longitudinal side of the intervening layer facing toward the central axis of the bone tunnel and the second longitudinal side of the intervening layer facing toward the rigid portion of the host bone; and
   compressing the intervening layer of bone against a graft ligament positioned within the bone tunnel.

* * * * *